US007038044B1

(12) United States Patent
Aulombard et al.

(10) Patent No.: US 7,038,044 B1
(45) Date of Patent: May 2, 2006

(54) METHOD FOR PREPARING 2-(2-ARYLMORPHOLIN-2-YL)ETHANOL DERIVATIVES AND INTERMEDIATES

(75) Inventors: Alain Aulombard, Lattes (FR); Françoise Bernon, Saint Gély du Fesc (FR); Sabrina Bonnefoy, Sommieres (FR); Alain Burgos, Exton, PA (US); Claude Cabos, Juvignac (FR); Eric Lucas, La Boissiere (FR)

(73) Assignee: sanofi-aventis, Paris (FR)

( * ) Notice: Subject to any disclaimer, the term of this patent is extended or adjusted under 35 U.S.C. 154(b) by 0 days.

(21) Appl. No.: 10/030,600

(22) PCT Filed: Jul. 7, 2000

(86) PCT No.: PCT/FR00/01966

§ 371 (c)(1),
(2), (4) Date: Apr. 1, 2002

(87) PCT Pub. No.: WO01/04105

PCT Pub. Date: Jan. 18, 2001

(30) Foreign Application Priority Data

Jul. 9, 1999  (FR) .................................. 99 09061

(51) Int. Cl.
*C07D 265/30* (2006.01)

(52) U.S. Cl. ..................................... 544/170

(58) Field of Classification Search ................. 544/170
See application file for complete search history.

(56) References Cited

U.S. PATENT DOCUMENTS

| 5,616,777 | A | * | 4/1997 | Andrews et al. ............... 560/29 |
| 5,641,777 | A | | 6/1997 | Emonds-Alt et al. |
| 5,780,466 | A | | 7/1998 | Emonds-Alt et al. |

FOREIGN PATENT DOCUMENTS

| WO | WO 96 23787 A | 8/1996 |
| WO | WO 99 28307 A | 6/1999 |
| WO | WO 00 39072 A | 7/2000 |

OTHER PUBLICATIONS

Takahide, N. et al; Tetrahedron: Assymmetry, No. 9, (1998) pp. 3251-3262.
K.A. Van Houten et al; J. of the American Chemical Society; vol. 120, No. 24, 1998, pp. 5864-5872.
Beilstein Informationssysteme GmbH; Abstract No. XP002150501, 1989.
Derwent Patent Abstract No. 199931 (2001).

* cited by examiner

*Primary Examiner*—Joseph K. McKane
*Assistant Examiner*—Rebecca Anderson
(74) *Attorney, Agent, or Firm*—Balaram Gupta

(57) ABSTRACT

The invention relates to a process for the preparation of substituted 2-(2-arylmorpholin-2-yl)ethanol derivatives.

2 Claims, No Drawings

METHOD FOR PREPARING 2-(2-ARYLMORPHOLIN-2-YL)ETHANOL DERIVATIVES AND INTERMEDIATES

The present application is a 371 of PCT/FR00/01966 filed 7 Jul. 2000.

A subject matter of the present invention is novel processes for the preparation of substituted 2-(2-arylmorpholin-2-yl)ethanol derivatives in the enantiomerically pure form and intermediate compounds of use in these processes.

Substituted 2-(2-arylmorpholin-2-yl)ethanol derivatives of formula:

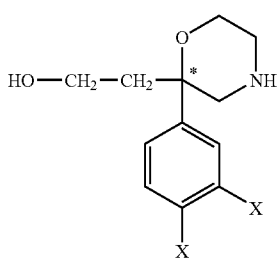

(I)

in which X represents a halogen atom and * indicates the position of the asymmetric carbon atom, are key intermediates in the preparation of tachykinin receptor antagonist compounds, such as those disclosed in international application WO 96/23787 and in application EP-A-776 893. Thus, for example, (R)-(+)-3-{1-[2-(4-benzoyl-2-(3,4-difluorophenyl)morpholin-2-yl)ethyl]-4-phenylpiperidin-4-yl}-1,1-dimethylurea is described as a powerful and selective antagonist for human $NK_2$ receptors of neurokinin A (X. Emonds-Alt et al., Neuropeptides, 1997, 31 (5), 449–458) and, consequently, may be of use in particular in the treatment of conditions of the respiratory, gastrointestinal, urinary, immune or cardiovascular system, and of the central nervous system, and of pain and migraine.

The term "halogen atom" is understood to mean a bromine, chlorine, fluorine or iodine atom.

Preferably, a subject matter of the present invention is novel processes for the preparation of enantiomerically pure compounds of formula (I) in which X represents a chlorine atom or a fluorine atom.

The preparation of compounds of formula (I) is illustrated in international application WO 96/23787 and is carried out according to scheme 1 below, in which X represents a halogen atom.

SCHEME 1

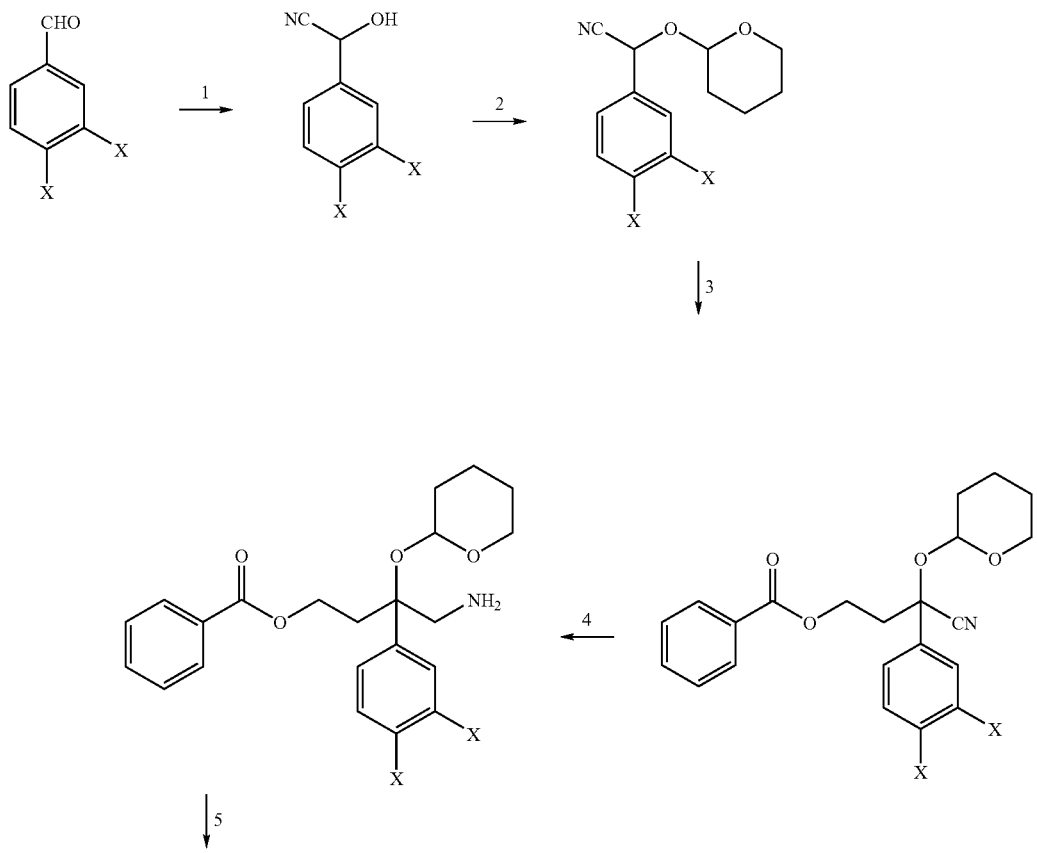

-continued

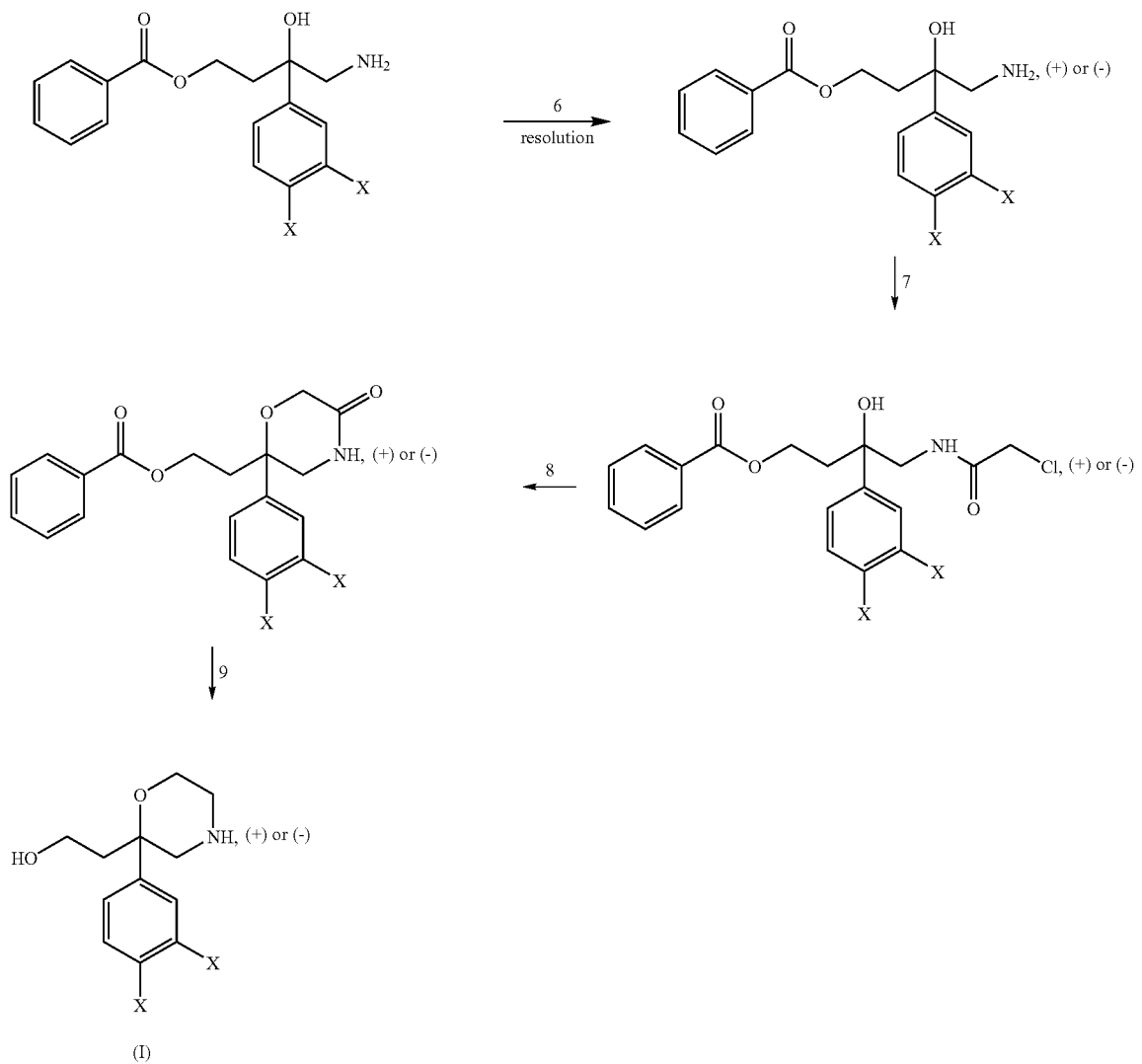

However, this process has disadvantages which are sufficient to exclude it from any use on an industrial scale.

For example, the compound of formula (I) in which X represents a fluorine atom prepared by this process is obtained with a very low yield, of the order of 1 to 2% calculated from the starting benzaldehyde derivative, from the description of application WO 96/23787.

The compound of formula (I) in which X represents a chlorine or fluorine atom can also be prepared according to the enantioselective process described in Tetrahedron: Asymmetry, 1998, 9, 3251–3262. However, this process has the disadvantage of using starting materials, such as diketene, and reagents, such as dichlorobis(triphenylphosphine)-palladium(II), AD-mix-□® or diethyl azodicarboxylate, the costs of which render the production of compound of formula (I) highly expensive on an industrial scale.

Novel processes for the preparation of the enantiomerically pure compound of formula (I) from simple starting materials and reagents and with yields of the order of 5 to 25% have now been found.

Thus, according to one of its aspects, a subject matter of the present invention is a process A for the preparation of a compound, in the enantiomerically pure form, of formula:

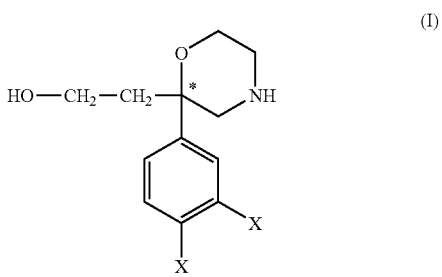

(I)

in which X represents a halogen atom, of its salts with inorganic or organic acids or of its salts with optically active organic acids, characterized in that:

a) a compound, in the racemic form, in the form of a mixture of diastereoisomers or in the enantiomerically pure form, of formula:

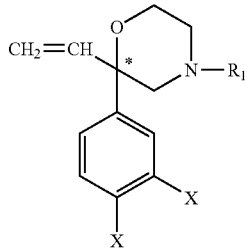

(II): (IIa):

(IIb):
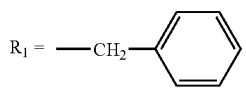

(IIc):
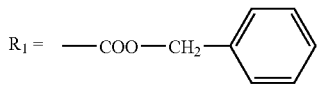

(IId):
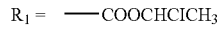
R₁ = —COOCHClCH₃

(IIe):
R₁ = —COO—C(CH₃)₃

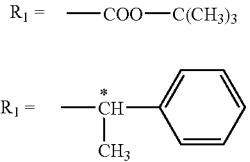

in which X is as defined for a compound of formula (I) and R₁ represents an N-protecting group chosen from a benzyl group, a benzyloxycarbonyl group, a 1-chloro-ethyloxycarbonyl group, a tert-butyloxycarbonyl group or an α-methylbenzyl group, is converted to a compound, in the racemic form, in the form of a mixture of diastereoisomers or in the enantiomerically pure form, of formula:

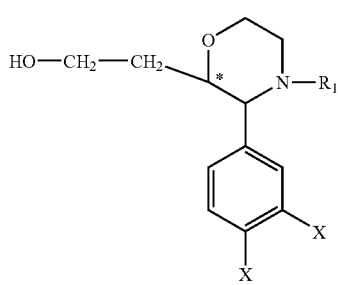

(III): (IIIa):

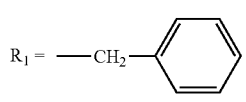

(IIIb):
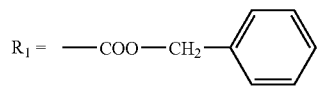

(IIIc):
R₁ = —COOCHClCH₃

(IIId):
R₁ = —COO—C(CH₃)₃

(IIIe):

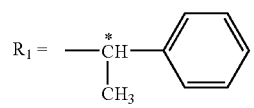

b) the compound of formula (III) thus obtained is deprotected;

C) if appropriate, when the compound of formula (I) thus obtained is in the racemic form, the enantiomers are separated, and, optionally, the enantiomerically pure compound of formula (I) is converted to one of its salts with inorganic or organic acids.

Preferably, in process A, R₁ represents a benzyl group or a benzyloxycarbonyl group.

When X represents a chlorine atom, preferably, in process A, R₁ represents a tert-butyloxycarbonyl group or a 1-chloroethyloxycarbonyl group.

When, in process A according to the invention, non-racemizing reactions which retain the chirality are used in stages a) and b), an enantiomerically pure compound of formula (I) is prepared directly using, as starting compound, an enantiomerically pure compound of formula (II).

In stage a) of process A, a compound of formula (II) is converted to a compound of formula (III) according to conventional methods well known to a person skilled in the art.

Preferably, in stage a), the compound of formula (II) is first subjected to a hydroboration reaction and then to an oxidation reaction to obtain a compound of formula (III).

The hydroboration reaction of an asymmetric alkene of formula (II) and then the in situ oxidation reaction of the organoborane formed as an intermediate to give the primary alcohol of formula (III) are carried out according to conventional methods, such as those described in J. Am. Chem. Soc., 1974, 96 (25), 7765–7770 or in J. Am. Chem. Soc., 1960, 82, 4708–4712.

The hydroboration agents used, which are well known to a person skilled in the art, are, for example, either borane complexes, such as the borane-tetrahydrofuran complex or the borane-dimethyl sulfide complex, or 9-borabicyclo [3.3.1]nonane or 9-BBN. The borane used can also be generated in situ, according to conventional methods, from, for example, sodium borohydride or lithium borohydride and an acid, such as a Lewis acid.

Use is preferably made of the borane-tetrahydrofuran complex, 9-borabicyclo[3.3.1]nonane or the borane generated in situ by reaction of trimethylsilyl chloride with sodium borohydride.

When the borane-tetrahydrofuran complex is used, the latter participates in the reaction in a proportion of 0.3 to 1.5 molar equivalents per molar equivalent of compound of formula (II).

When 9-borabicyclo[3.3.1]nonane is used, the latter participates in the reaction in a proportion of 1 to 1.5 molar equivalents per molar equivalent of compound of formula (II).

When the borane is generated in situ by reaction of trimethylsilyl chloride with sodium borohydride, these compounds are each used in a proportion of 3 to 5 molar equivalents per molar equivalent of compound of formula (II).

The hydroboration reaction is carried out in an inert solvent, such as an ether, for example diethyl ether, tetrahydrofuran, dioxane, dimethoxyethane or diethylene glycol dimethyl ether, or such as an aromatic hydrocarbon, for example toluene or xylene, at a temperature of between ambient temperature and the reflux temperature of the solvent and for a time of between 5 and 48 hours.

The organoborane formed as an intermediate substance is subsequently subjected to a conventional oxidation reaction. Preferably, the oxidation reaction is carried out under phase transfer catalysis conditions using a peroxide, in the presence of a strong base and of a phase transfer catalyst in an inert solvent and water.

It is preferable to use hydrogen peroxide as peroxide. Hydrogen peroxide participates in the reaction in a proportion of 3 to 5 molar equivalents per molar equivalent of compound of formula (II).

The base used during the reaction is chosen from an alkali metal hydroxide, such as sodium hydroxide. It participates in the reaction in a proportion of 1 to 2 molar equivalents per molar equivalent of compound of formula (II).

The phase transfer catalyst is chosen from substituted quaternary ammonium salts, such as tetrabutylammonium hydrogensulfate. It participates in the reaction in a proportion of 0.01 to 0.1 molar equivalent per molar equivalent of compound of formula (II).

The oxidation reaction is carried out in one of the solvents abovementioned above for the hydroboration reaction and at a temperature of between 0° C. and 60° C.

This oxidation reaction is highly exothermic and requires control of the flow rate for introduction of the peroxide and of the temperature of the reaction medium.

The reaction takes place over a time of between the duration of introduction of the hydrogen peroxide solution and 48 hours.

As the hydrogen peroxide/tetrahydrofuran mixture is regarded as dangerous at the industrial stage, it is preferable to carry out the oxidation reaction in an aromatic solvent, preferably toluene. In this case, an exchange of solvent may be necessary before the oxidation reaction or, preferably, before the hydroboration reaction.

In stage b) of process A, the compound of formula (III) thus obtained is deprotected according to conventional methods.

Thus, the deprotection of the benzyl group of the compound of formula (IIIa), the deprotection of the benzyloxycarbonyl group of the compound of formula (IIIb) or the deprotection of the α-methylbenzyl group of the compound of formula (IIIe) is carried out by hydrogenolysis, preferably by catalytic hydrogenation, or by hydrogen transfer catalysis.

The catalytic hydrogenation is carried out in an inert solvent, such as an alcohol (methanol, ethanol or propan-2-ol, for example), an aromatic hydrocarbon (toluene or xylene, for example) or an ester (ethyl acetate, for example), or in a mixture of these abovementioned solvents, in the presence of a catalyst, such as palladium-on-charcoal or Raney nickel, under a pressure of between 1 and 10 bar, at a temperature of between 0° C. and 100° C. and for a time of between 1 and 24 hours.

The hydrogen transfer catalysis is carried out using ammonium formate in the presence of a catalyst, such a palladium-on-charcoal, in an inert solvent, such as an alcohol (methanol or ethanol, for example), at a temperature of between ambient temperature and the reflux temperature of the solvent and for a time of between 2 and 48 hours.

The deprotection of the 1-chloroethyloxy-carbonyl group of the compound of formula (IIIc) is carried out by reaction with methanol at a temperature of between ambient temperature and the reflux temperature of the solvent.

The deprotection of the tert-butyloxycarbonyl group of the compound of formula (IIId) is carried out by acid hydrolysis by means of hydrochloric acid or trifluoroacetic acid, for example, in an inert solvent, such as an alcohol (methanol or ethanol, for example), an ether (diethyl ether, dioxane or tetrahydrofuran, for example) or a halogenated hydrocarbon (dichloromethane, for example), and at a temperature of between −10° C. and the reflux temperature of the solvent.

When the compound of formula (I) is obtained in the racemic form, the enantiomers are separated in stage c) according to known methods. Preferably, the separation is carried out by preparation of an optically active salt, by the action of an optically active organic acid, such as L-(+)- or D-(−)-mandelic acid, L-(−)- or D-(+)-di-para-toluoyltartaric acid, L-(+)- or D-(−)-tartaric acid, L-(−)- or D-(+)-dibenzoyltartaric acid or (1R)-(−)- or (1S)-(+)-10-camphorsulfonic acid, and then separation of the isomers, for example by crystallization. The desired enantiomer is released from its salt in basic medium.

Preferably, the separation of the enantiomers of the compound of formula (I) is carried out by formation of an optically active salt, by the action of L-(−)- or D-(+)-di-para-toluoyltartaric acid.

The enantiomerically pure compounds of formula (I) in the form of optically active salts with optically active organic acids are novel and form part of the invention.

The enantiomerically pure compounds of formula (I) in the form of optically active salts with optically active organic acids in which X represents a chlorine atom or a fluorine atom are preferred.

The enantiomerically pure compounds of formula (I) in the form of salts with L-(−)- or D-(+)-di-para-toluoyltartaric acid are preferred.

The compounds of formula (II), in the enantiomerically pure form, in the racemic form or in the form of a mixture of diastereoisomers, and their optional salts with inorganic or organic acids are novel and form part of the invention.

The compounds of formula (II) in which X represents a chlorine atom or a fluorine atom are preferred.

The compounds of formula (II) in which $R_1$ represents a benzyl group or a benzyloxycarbonyl group are preferred.

According to another of its aspects, a subject matter of the invention is a process B for the preparation of a compound, in the enantiomerically pure form or in the racemic form, of formula:

(II): (IIb):

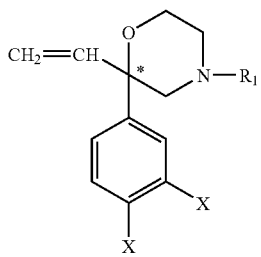

(IIc):

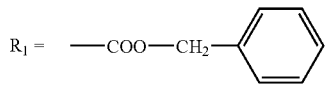

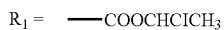

in which X represents a halogen atom and $R_1$ represents a benzyloxycarbonyl group or a 1-chloroethyloxycarbonyl group, characterized in that a compound, in the enantiomerically pure form or in the racemic form, of formula:

(IIa)

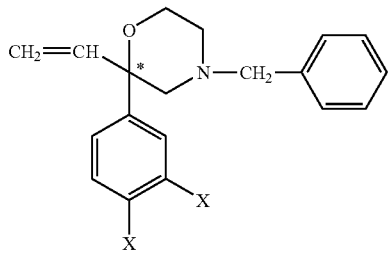

in which X is as defined for a compound of formula (II), is reacted with benzyl chloroformate or 1-chloroethyl chloroformate in the presence of a base, with or without solvent.

Preferably, in process B, $R_1$ represents a benzyloxycarbonyl group.

The benzyl chloroformate or the 1-chloroethyl chloroformate is used in the reaction in a proportion of 1 to 1.5 molar equivalents per molar equivalent of compound of formula (IIa).

The base used in the reaction is chosen from organic bases, such as triethylamine, N,N-diisopropyl-ethylamine or N-methylmorpholine, or from alkali metal carbonates or bicarbonates, such as sodium carbonate, potassium carbonate or sodium bicarbonate.

The base is used in the reaction in a proportion of 0.01 to 1.5 molar equivalents per molar equivalent of compound of formula (IIa).

When the reaction is carried out in a solvent, the latter is chosen from an aromatic hydrocarbon, such as toluene or xylene, a halogenated hydrocarbon, such as dichloromethane, 1,2-dichloro-ethane, carbon tetrachloride, chlorobenzene or dichlorobenzene, an ether, such as tetrahydrofuran, dioxane or dimethoxyethane, an ester, such as ethyl acetate, an amide, such as N,N-dimethylformamide, a nitrile, such as acetonitrile, or a ketone, such as acetone.

The reaction is carried out at a temperature of between −20° C. and the reflux temperature of the solvent and for a time of between 1 to 24 hours.

According to another of its aspects, a subject matter of the invention is a process C for the preparation of a compound, in the enantiomerically pure form, in the form of a mixture of diastereoisomers or in the racemic form, of formula:

(II): (IIa):

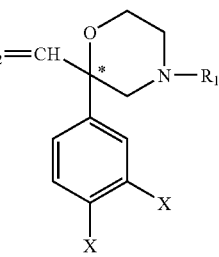

(IId):

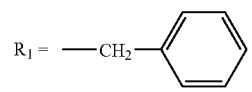

(IIe):

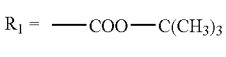

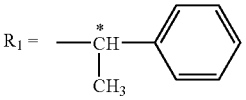

in which X represents a halogen atom and $R_1$ represents a benzyl group, a tert-butyloxycarbonyl group or an α-methylbenzyl group, of its optional salts with inorganic or organic acids, characterized in that a compound, in the enantiomerically pure form, in the form of a mixture of diastereoisomers or in the racemic form, of formula:

(IV): (IVa):

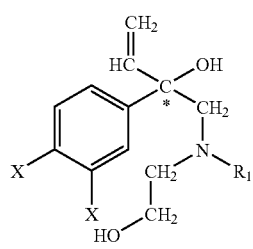

(IVd):

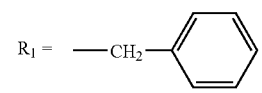

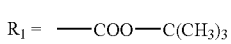

-continued (IVe):

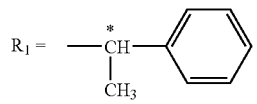

in which X and $R_1$ are as defined for a compound of formula (II), is cyclized and, optionally, the compound of formula (II) thus obtained is converted to one of its salts.

Preferably, in process C, $R_1$ represents a benzyl group.

The reaction for the cyclization of a diol of formula (IV) to a morpholine derivative of formula (II) can be carried out according to known methods as described, for example, in J. Med. Chem., 1994, 37, 2791–2796.

Preferably, the cyclization reaction is carried out under phase transfer catalysis conditions using an alkylsulfonyl or arylsulfonyl halide in the presence of a strong base and of a phase transfer catalyst, in an inert solvent as a mixture with water.

The reaction of the primary alcohol of the compound of formula (IV) with an alkylsulfonyl or arylsulfonyl halide in the presence of a strong base makes it possible first to form an alkylsulfonate or arylsulfonate ester which, under the reaction conditions, cyclizes in situ to form the morpholine ring.

It has been found that, when the cyclization reaction of an enantiomerically pure compound of formula (IV) is carried out under the abovementioned conditions, an enantiomerically pure compound of formula (II) is obtained, the asymmetric carbon of which has the same configuration.

Preference is given, among alkylsulfonyl or arylsulfonyl halides, to methanesulfonyl chloride, benzenesulfonyl chloride or p-toluenesulfonyl chloride.

The alkylsulfonyl or arylsulfonyl halide participates in the reaction in a proportion of 1 to 1.5 molar equivalents per molar equivalent of compound of formula (IV).

The base used during the reaction is chosen from an alkali metal hydroxide, such as sodium hydroxide or potassium hydroxide.

The base participates in the reaction in a proportion of 5 to 10 molar equivalents per molar equivalent of compound of formula (IV).

The phase transfer catalyst is chosen from substituted quaternary ammonium salts, such as benzyltriethylammonium chloride.

The catalyst participates in the reaction in a proportion of 0.01 to 0.1 molar equivalent per molar equivalent of compound of formula (IV).

The reaction is carried out in an inert solvent, such as an aromatic hydrocarbon, for example toluene or xylene.

The reaction is carried out at a temperature of between ambient temperature and 60° C. and takes place over a period of 1 to 24 hours.

The compound of formula (IV), in the enantiomerically pure form, in the form of a mixture of diastereoisomers or in the racemic form, and its optional salts with inorganic or organic acids are novel and form part of the invention.

The compound of formula (IV) in which X represents a chlorine atom or a fluorine atom is preferred.

The compound of formula (IV) in which $R_1$ represents a benzyl group is preferred.

According to another of its aspects, a subject matter of the invention is a process D for the preparation of a compound, in the enantiomerically pure form, of formula:

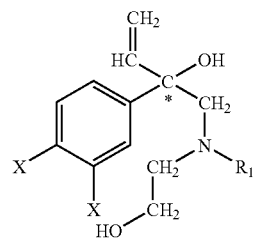

(IV): (IVa):

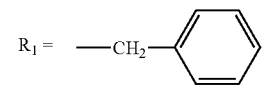

(IVe):

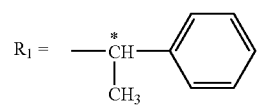

in which X represents a halogen atom and $R_1$ represents a benzyl group or an α-methylbenzyl group, of its salts with inorganic or organic acids, characterized in that:

a) a compound, in the racemic form, of formula:

(V)

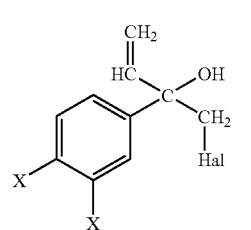

in which X is as defined for a compound of formula (IV) and Hal represents a halogen atom, is reacted with benzylamine or with R-(+)- or S-(–)-α-methylbenzylamine in the presence of a base in an inert solvent, to produce a compound, in the racemic form or in the form of a mixture of diastereomers, of formula:

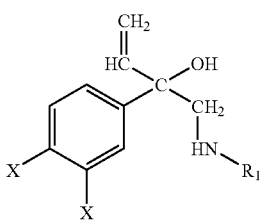

-continued (VI): (VIa):

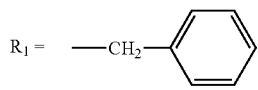

(VIe):

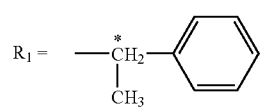

b) the enantiomers or the diastereoisomers of the compound of formula (VI) thus obtained are separated;

C) the enantiomerically pure compound of formula (VI) is reacted:

either with ethylene oxide in the catalytic presence of an acid in an inert solvent;

or with a compound of formula Hal'''—$CH_2$—$CH_2$—O—$R_2$ (XXI), in which $R_2$ represents an O-protecting group and Hal'''' represents a halogen atom, in the presence of a base in an inert solvent, followed by the deprotection of the O-protecting group;

and, optionally, the enantiomerically pure compound of formula (IV) is converted to one of its salts with inorganic or organic acids.

Preferably, in process D, $R_1$ represents a benzyl group.

Preferably, in stage a) of process D, use is made of a compound of formula (V) in which Hal represents a chlorine or bromine atom.

In stage a) of process D, the compound of formula (V) is first converted to an intermediate epoxide derivative of formula:

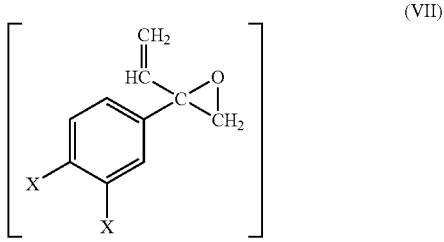

(VII)

which, under the reaction conditions, reacts with the amine to give the compound of formula (VI).

The amine participates in the reaction in a proportion of 1 to 1.5 molar equivalents per molar equivalent of compound of formula (V).

The base used in the reaction is chosen from alkali metal carbonates or bicarbonates, such as sodium carbonate, potassium carbonate or sodium bicarbonate. Preferably, sodium bicarbonate is used.

The base participates in the reaction in a proportion of 1 to 2 molar equivalents per molar equivalent of compound of formula (V).

The inert solvent is chosen from polar solvents, such as acetonitrile, propionitrile or 1-methyl-2-pyrrolidinone. Propionitrile constitutes a preferred solvent.

The reaction is carried out at a temperature of between 80° C. and 120° C.

The reaction is carried out over a period of 5 to 24 hours.

In stage b) of process D, the enantiomers of the compound of formula (VIa) thus obtained are separated according to conventional methods. Preferably, the separation can be carried out by preparation of an optically active salt by the action of an optically active organic acid, such as L-(+)- or D-(−)-mandelic acid, L-(−)- or D-(+)-di-para-toluoyltartaric acid, L-(+)- or D-(−)-tartaric acid or L-(−)- or D-(+)-dibenzoyltartaric acid, and then separation of the isomers, for example by crystallization. The desired enantiomer is released from its salt in basic medium.

Preferably, the separation of the enantiomers of the compound of formula (VIa) is carried out by formation of an optically active salt by the action of L-(+)- or D-(−)-mandelic acid.

In stage b) of process D, the diastereoisomers of the compound of formula (VIb) thus obtained are separated according to conventional methods. Preferably, the separation can be carried out by preparation of a salt with an inorganic or organic acid or with an optically active organic acid, such as those mentioned above, and then separation of the diastereoisomers, for example by crystallization. The desired diastereoisomer can be released from its salt in basic medium.

In stage c) of process D, the reaction of the enantiomerically pure compound of formula (VI) with ethylene oxide is carried out in a reactor of hydrogenator type, since, at the temperatures used, ethylene oxide is in the gaseous form.

The ethylene oxide participates in the reaction in a proportion of 5 to 15 molar equivalents per molar equivalent of compound of formula (VI).

The solvent can, for example, be an alcohol, such as methanol.

The acid used in a catalytic amount in the reaction is chosen from conventional inorganic or organic acids, such as hydrochloric acid or acetic acid.

It has been found that the reaction between the compound of formula (VI) and ethylene oxide can be carried out without acid catalysis by using, as starting compound, the enantiomerically pure compound of formula (VI) in the form of a salt with an optically active acid, preferably with L-(+)- or D-(−)-mandelic acid.

The reaction is carried out at a temperature of between 0° C. and 60° C. and is carried out for a time of between 2 and 24 hours.

According to the other alternative of stage c) of process D, the protecting group $R_2$ is chosen from conventional O-protecting group well known to a person skilled in the art, such as the tetrahydropyran-2-yl group.

Use is preferably made of a compound of formula (XXI) in which Hal'''' represents a chlorine or bromine atom.

The compound of formula (XXI) participates in the reaction in a proportion of 1 to 2 molar equivalents per molar equivalent of the compound of formula (VI).

The base used in the reaction is chosen from alkali metal carbonates or bicarbonates, such as sodium carbonate, potassium carbonate or sodium bicarbonate.

The base participates in the reaction in a proportion of 1 to 2 molar equivalents per molar equivalent of the compound of formula (VI).

The inert solvent is chosen from polar solvents, such as acetonitrile, propionitrile or 1-methyl-2-pyrrolidone.

The reaction is carried out at a temperature of between 80° C. and 120° C. and is carried out over a period of 5 to 24 hours.

The deprotection of the O-protecting group $R_2$ is carried out according to methods known to a person skilled in the art. For example, when $R_2$ represents a tetrahydropyran-2-yl group, the deprotection is carried out by acid hydrolysis using an acid, such as hydrochloric acid.

The reaction is carried out in an ethereal solvent, such as diethyl ether, or an alcohol, such as methanol, or in an aromatic solvent, such as toluene, at a temperature of between 0° C. and the reflux temperature of the solvent and for a time of between 1 and 24 hours.

The compound of formula (VI), in the racemic form, in the form of a mixture of diastereoisomers or in the enantiomerically pure form, and its salts with inorganic or organic acids or its salts with optically active acids are novel and form part of the invention.

The enantiomerically pure compound of formula (VIa) in the form of a salt with L-(+)- or D-(−)-mandelic acid is preferred.

The compound of formula (VI) in which X represents a chlorine or fluorine atom is preferred.

The compound of formula (VI) in which $R_1$ represents a benzyl group is preferred.

The compound of formula (XXI) is prepared by protection of 2-haloethanol derivatives according to conventional methods, such as those described in Protective Groups in Organic Chemistry, J. F. W. McOmie, published by Plenum Press, 1973 and in Protective Groups in Organic Synthesis, T. W. Greene and P. G. M. Wutts, published by John Wiley and Sons, 1991.

According to another of its aspects, a subject matter of the invention is a process E for the preparation of a compound, in the racemic form or in the form of mixture of diastereoisomers, of formula:

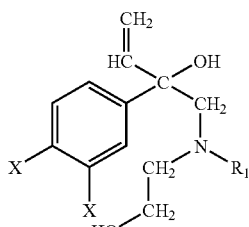

(IV): (IVa):

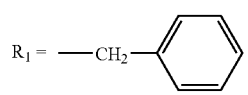

(IVd):

(IVe):

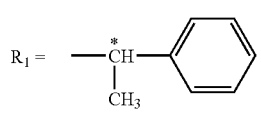

in which X represents a halogen atom and $R_1$ represents the benzyl group, the tert-butyloxycarbonyl group or the α-methylbenzyl group, of its optional salts with inorganic or organic acids, characterized in that:

a) a compound, in the racemic form, of formula:

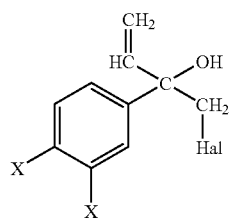

in which X is as defined for a compound of formula (IV) and Hal represents a halogen atom, is reacted either with 2-(benzylamino)-1-ethanol or with 2-amino-1-ethanol or with (R)- or (S)-2-(α-methylbenzylamino)-1-ethanol in the presence of a base and in an inert solvent, and, optionally, the compound of formula (IVa) or (IVe) thus obtained is converted to one of its salts with inorganic or organic acids;

b) if appropriate, when the compound of formula (V) is employed with 2-amino-1-ethanol in stage a), the compound thus obtained, of formula:

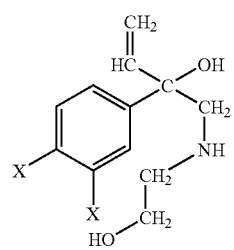

is treated with di-tert-butyl dicarbonate in the presence of a base and in an inert solvent to produce the compound of formula (IVd).

Preferably, in process E, $R_1$ represents a benzyl group.

Preferably, in stage a) of process E, use is made of a compound of formula (V) in which Hal represents a chlorine or bromine atom.

As in stage a) of process D, the compound of formula (V) is first converted to an intermediate epoxide derivative of formula (VII) which, under the reaction conditions, reacts in situ with the aminoethanol derivative to give the compound of formula (IVa), (IVe) or (IV'd).

The aminoethanol derivative participates in the reaction in a proportion of 1 to 1.5 molar equivalents per molar equivalent of compound of formula (V).

The base used in the reaction is chosen from alkali metal carbonates or bicarbonates, such as sodium carbonate, potassium carbonate or sodium bicarbonate. Preferably, sodium bicarbonate is used.

The base participates in a proportion of 1 to 2 molar equivalents per molar equivalent of compounds of formula (V).

The inert solvent is chosen from polar solvents, such as acetonitrile, propionitrile or 1-methyl-2-pyrrolidinone. 1-Methyl-2-pyrrolidinone constitutes a preferred solvent.

The reaction is carried out at a temperature of between 80 and 120° C. and for a time of between 10 and 24 hours.

If appropriate, in stage b) of process E, the compound of formula (IV'd) is reacted with di-tert-butyl dicarbonate in the presence of an organic base, such as triethylamine, N,N- diisopropylethylamine or N-methylmorpholine, in an inert solvent, such as dichloromethane, tetrahydrofuran or N,N-dimethyl-formamide, and at a temperature of between 0° C. and 60° C.

(R)- or (S)-2-(α-Methylbenzylamino)-1-ethanol is prepared according to the method described in J. Am. Chem. Soc., 1984, 106, 747–754.

The compounds of formula (V) are novel and form part of the invention.

The compound of formula (V) in which X represents a chlorine atom or a fluorine atom and Hal represents a chlorine or bromine atom is preferred.

According to another of its aspects, a subject matter of the invention is a process F for the preparation of a compound of formula:

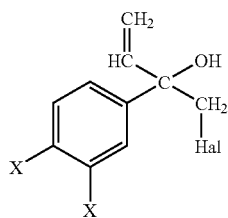
(V)

in which X represents a halogen atom and Hal represents a halogen atom, characterized in that:

a) a compound of formula:

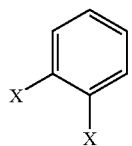
(VIII)

in which X is as defined for a compound of formula (V), is reacted with a compound of formula:

Hal'—CO—CH$_2$—Hal    (IX)

in which Hal' and Hal represent a halogen atom, in the presence of a Lewis acid and in an inert solvent, to produce a compound of formula:

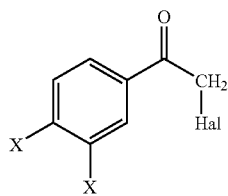
(X)

b) the compound of formula (X) thus obtained is reacted with a compound of formula:

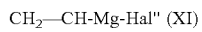
CH$_2$=CH—Mg—Hal"    (XI)

in which Hal" represents a halogen atom, in an inert solvent, followed by hydrolysis, and the expected compound of formula (V) is obtained.

According to a preferred aspect, the invention relates to the preparation of a compound of formula (V) in which Hal represents a chlorine or bromine atom.

Preferably, in stage a), use is made of a compound of formula (IX) in which Hal' and Hal each independently represent a chlorine or bromine atom and, in stage b), use is made of a compound of formula (XI) in which Hal' represents a chlorine or bromine atom.

Stage a) of process F is a Friedel-Crafts reaction carried out under Perrier conditions according to conventional methods.

The Lewis acid is chosen from conventional Lewis acids; preferably aluminum chloride is used.

The Lewis acid is used in the reaction in a proportion of 1 to 1.5 molar equivalents per molar equivalent of compound of formula (VIII).

Preference is given, among haloacetyl halides of formula (IX), to the use of chloroacetyl chloride.

The compound of formula (IX) is used in a proportion of 1 to 1.5 molar equivalents per molar equivalent of compound of formula (VIII).

The solvent is chosen from aromatic hydrocarbons, such as toluene or xylene, chlorinated hydrocarbons, such as dichloromethane, dichloroethane, carbon tetrachloride, chlorobenzene or dichlorobenzene, or ethers, such as tetrahydrofuran, dioxane or dimethoxyethane. Preferably, dichloromethane is used.

The reaction is carried out at a temperature of between 0° C. and 100° C. and for a time of between 1 and 24 hours.

Stage b) of process F is a Grignard reaction carried out according to conventional methods.

The compound of formula (XI) is used in the reaction in a proportion of 1 to 1.5 molar equivalents per molar equivalent of compound of formula (X).

The solvent is chosen from ethers, such as diethyl ether, diisopropyl ether, tetrahydrofuran or dioxane. Preferably, tetrahydrofuran is used.

The reaction is carried out at a temperature of between –20° C. and 0° C. and for a time of between 1 and 24 hours.

At the end of the reaction, the reaction mixture is hydrolyzed according to conventional methods by pouring it, for example, onto a saturated ammonium chloride solution.

According to another of its aspects, a subject matter of the invention is a process G for the preparation of a compound, in the racemic form, of formula:

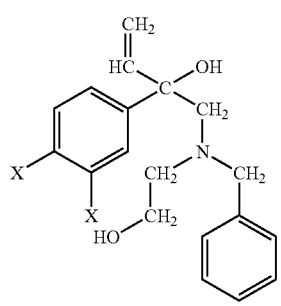
(IVa)

in which X represents a halogen atom, of its salts with inorganic or organic acids, characterized in that:

a) the preparation is carried out as in stage a) of process F;

b) the compound of formula (X) thus obtained is reacted with a compound of formula:

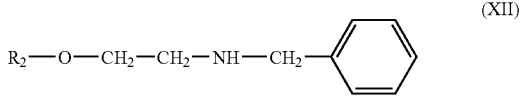

(XII)

in which $R_2$ represents an O-protecting group, in the presence of a base and in an inert solvent, to produce a compound of formula:

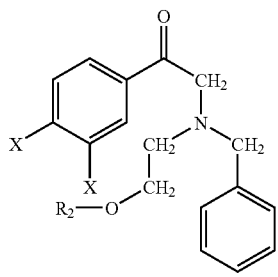

(XIII)

c) the compound of formula (XIII) thus obtained is reacted with a compound of formula:

$$CH_2=CH-Mg-Hal'' \qquad (XI)$$

in which Hal" represents a halogen atom, in an inert solvent, followed by hydrolysis, to produce a compound of formula:

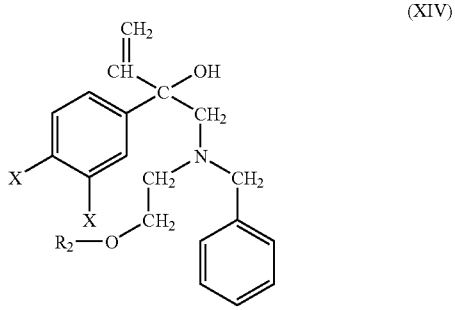

(XIV)

d) the compound of formula (XIV) is deprotected and, optionally, the compound of formula (IVa) thus obtained is converted to one of its salts with inorganic or organic acids.

Preferably, in stage a), use is made of a compound of formula (IX) in which Hal' and Hal each independently represent a chlorine or bromine atom.

In stage b) of process G, the protecting group $R_2$ is chosen from conventional O-protecting groups well known to a person skilled in the art, such as the tetrahydropyran-2-yl group.

The compound of formula (XII) participates in the reaction in a proportion of 1 to 1.5 molar equivalents per molar equivalent of compound of formula (X).

The base is chosen from alkali metal carbonates or bicarbonates, preferably sodium bicarbonate.

The base is used in a proportion of 1 to 1.5 molar equivalents per molar equivalent of compound of formula (X).

The inert solvent is chosen from polar solvents, such as acetonitrile or propionitrile, or ethers, such as tetrahydrofuran, or halogenated solvents, such as dichloromethane. Preferably, tetrahydrofuran is used.

The reaction is carried out at a temperature of between ambient temperature and the reflux temperature of the solvent and for a time of between 1 and 24 hours.

Stage c) of process G is a Grignard reaction carried out according to conventional methods.

Preferably, in stage c), use is made of a compound of formula (XI) in which Hal" represents a chlorine or bromine atom.

The compound of formula (XI) is used in the reaction in a proportion of 1.5 to 2 molar equivalents per molar equivalent of compound of formula (XIII).

The solvent is chosen from ethers, such as diethyl ether, diisopropyl ether, tetrahydrofuran or dioxane. Preferably, use is made of tetrahydrofuran.

The reaction is carried out at a temperature of between ambient temperature and the reflux temperature of the solvent and takes place for a time of between 1 and 24 hours.

At the end of the reaction, the reaction mixture is hydrolyzed by pouring it, for example, onto a saturated ammonium chloride solution.

The compound of formula (XIV) is deprotected in stage d) of process G according to methods known to a person skilled in the art. For example, when $R_2$ represents a tetrahydropyran-2-yl group, deprotection is carried out by acid hydrolysis using an acid, such as hydrochloric acid. The latter can be generated in situ from acetyl chloride and methanol.

The reaction is carried out in an ethereal solvent, such as diethyl ether, or an alcohol, such as methanol, at a temperature of between 0° C. and the reflux temperature of the solvent and for a time of between 1 and 24 hours.

The compound of formula (XIII) and its salts with inorganic or organic acids are novel and form part of the invention.

The compound of formula (XIII) in which X represents a chlorine or fluorine atom is preferred.

The compound of formula (XIV) and its salts with inorganic or organic acids are novel and form part of the invention.

The compound of formula (XIV) in which X represents a chlorine or fluorine atom is preferred.

The compound of formula (XII) is prepared by protection of the 2-(benzylamino)-1-ethanol according to conventional methods, such as those described in Protective Groups in Organic Chemistry, J. F. W. McOmie, published by Plenum Press, 1973 and in Protective Groups in Organic Synthesis, T. W. Greene and P. G. M. Wutts, published by John Wiley and Sons, 1991.

According to another of its aspects, a subject matter of the invention is an enantioselective process H for the preparation of a compound, in the enantiomerically pure form, of formula:

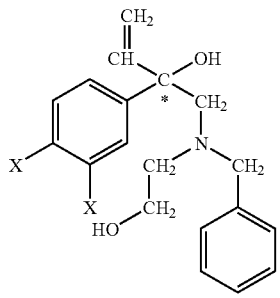

(IVa)

in which X represents a halogen atom, of its salts with inorganic or organic acids, characterized in that:
a) a compound of formula:

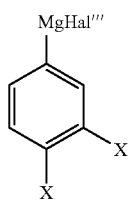

(XV)

in which X is as defined for a compound of formula (IVa) and Hal''' represents a halogen atom, is reacted with methyl (R)- or (S)-2-phenylhexahydropyrrolo-[1,2-c]imidazole-3-carboxylate, of formula:

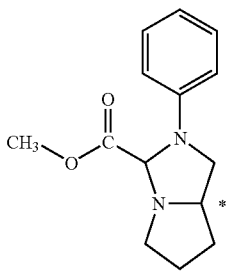

(XVI)

in the presence of magnesium chloride in an inert solvent, followed by hydrolysis, to produce a compound, in the enantiomerically pure form, of formula:

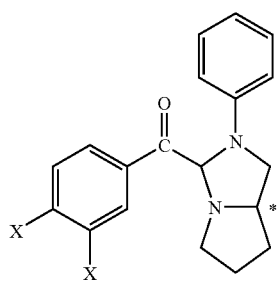

(XVII)

b) the compound of formula (XVII) thus obtained is reacted with a compound of formula:

$$CH_2=CH-Mg-Hal''$$ (XI)

in which Hal'' represents a halogen atom, in an inert solvent, followed by hydrolysis, to produce a compound, in the enantiomerically pure form, of formula:

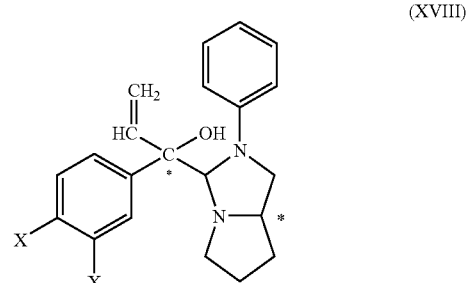

(XVIII)

c) the compound of formula (XVIII) thus obtained is hydrolyzed by the action of an acid in an inert solvent as a mixture with water, to produce a compound, in the enantiomerically pure form, of formula:

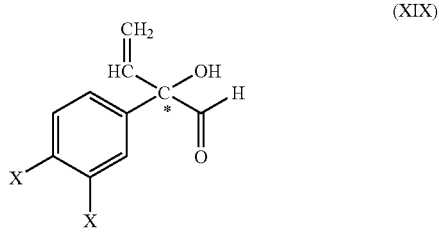

(XIX)

d) the compound of formula (XIX) thus obtained is reacted with 2-(benzylamino)-1-ethanol in the presence of an acid in an inert solvent, then the iminium salt formed as an intermediate is reduced by means of a reducing agent and, optionally, the enantiomerically pure compound of formula (IVa) is converted to one of its salts with inorganic or organic acids.

Preferably, in stage a), use is made of a compound of formula (XV) in which Hal''' represents a chlorine or bromine atom and, in stage b), use is made of a compound of formula (XI) in which Hal'' represents a chlorine or bromine atom.

Stages a), b) and c) of process H are carried out according to the method for asymmetric synthesis of α-hydroxyaldehydes described by T. Mukaiyama in Tetrahedron, 1981, 37 (23), 4111–4119.

In stage d), an α-hydroxyaldehyde of formula (XIX) is reacted with 2-(benzylamino)-1-ethanol in the presence of an acid, such as acetic acid, in a polar solvent, such as acetonitrile, to form in situ an intermediate imine which is reduced chemically using, for example, sodium triacetoxyborohydride or sodium cyanoborohydride or catalytically using hydrogen and a catalyst, such as palladium-on-charcoal.

The enantiomerically pure or racemic compound of formula (XIX) is novel and forms part of the invention.

The compound of formula (XIX) in which X represents a chlorine or fluorine atom is preferred.

According to another of its aspects, a subject matter of the invention is an enantioselective process I for the preparation of a compound, in the enantiomerically pure form, of formula:

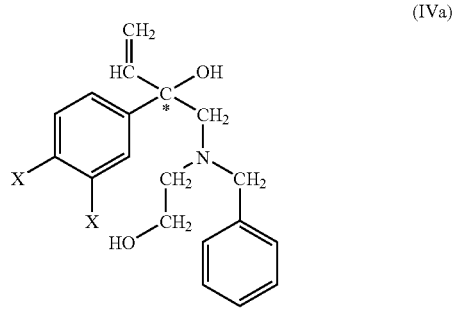

(IVa)

in which X represents a halogen atom, of its salts with inorganic or organic acids, characterized in that:
a)b)c) the preparation is carried out as in stages a), b) and c) of process H;
d) the compound of formula (XIX) thus obtained is reduced by means of a reducing agent in an inert solvent to produce an enantiomerically pure compound of formula:

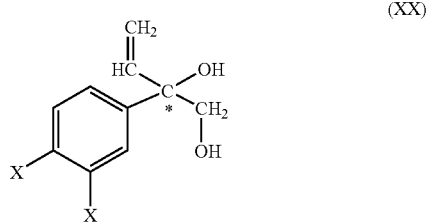

(XX)

e) the compound of formula (XX) thus obtained is cyclized to produce a compound, in the enantiomerically pure form, of formula:

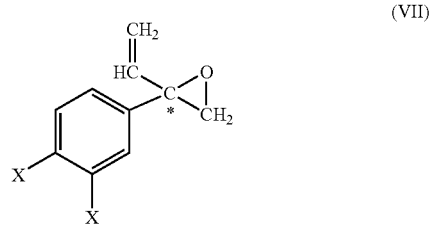

(VII)

f) the compound of formula (VII) thus obtained is reacted with 2-(benzylamino)-1-ethanol in the presence of a base and in an inert solvent and, optionally, the enantiomerically pure compound of formula (IVa) is converted to one of its salts with inorganic or organic acids.

In stage d), the reduction of the aldehyde of formula (XIX) to a diol of formula (XX) is carried out according to conventional methods using a reducing agent, such as sodium borohydride, diisobutylaluminum hydride or lithium aluminum hydride. Preferably, sodium borohydride is used.

The reaction is carried out in an inert solvent, such as an aromatic solvent, for example toluene, an alcohol, for example ethanol, an ether, for example tetrahydrofuran, or a mixture of these solvents.

The reaction is carried out at a temperature of between $-70°$ C. and the reflux temperature of the solvent and for a time of between 1 and 24 hours.

In stage e), the cyclization of a diol of formula (XX) to an oxirane derivative of formula (VII) is carried out, preferably, under phase transfer catalysis conditions using an alkylsulfonyl or arylsulfonyl halide in the presence of a strong base and of a phase transfer catalyst, in an inert solvent as a mixture with water.

It has been found that, when the cyclization reaction of an enantiomerically pure compound of formula (XX) is carried out under the abovementioned conditions, an enantiomerically pure compound of formula (VII) is obtained, the asymmetric carbon atom of which has the same configuration.

Preference is given, among alkylsulfonyl or arylsulfonyl halides, to methanesulfonyl chloride, benzenesulfonyl chloride or p-toluenesulfonyl chloride.

The alkylsulfonyl or arylsulfonyl halide participates in the reaction in a proportion of 1 to 1.5 molar equivalents per molar equivalent of compound of formula (XX).

The base used during the reaction is chosen from an alkali metal hydroxide, such as sodium hydroxide or potassium hydroxide.

The base participates in the reaction in a proportion of 5 to 10 molar equivalents per molar equivalent of compound of formula (XX).

The phase transfer catalyst is chosen from substituted quaternary ammonium salts, such as benzyltriethylammonium chloride.

The catalyst participates in the reaction [lacuna] of 0.01 to 0.1 molar equivalent per molar equivalent of compound of formula (XX).

The reaction is carried out in an inert solvent, such as an aromatic hydrocarbon, for example toluene or xylene, or a chlorinated solvent, for example dichloromethane.

The reaction is carried out at a temperature of between ambient temperature and $60°$ C. and for a time of between 1 and 24 hours.

In stage f), the opening of the oxirane derivative of formula (VII) by 2-(benzylamino)-1-ethanol is carried out according to conventional methods.

The amine participates in the reaction in a proportion of 1 to 1.5 molar equivalents per molar equivalent of compound of formula (VII).

The base is chosen from alkali metal carbonates or bicarbonates, such as sodium carbonate, potassium carbonate or sodium bicarbonate.

The base participates in the reaction in a proportion of 1 to 2 molar equivalents per molar equivalent of compound of formula (VII).

The solvent is chosen from polar solvents, such as acetonitrile, propionitrile or 1-methyl-2-pyrrolidinone.

The reaction is carried out at a temperature of between ambient temperature and $120°$ C. and for a time of between 1 to 48 hours.

It has been found that, when the reaction for opening the enantiomerically pure compound of formula (VII) is carried out under the abovementioned conditions, a compound of formula (IVa) is obtained in which the asymmetric carbon atom has the same configuration.

The enantiomerically pure or racemic compound of formula (XX) is novel and forms part of the invention.

The compound of formula (XX) in which X represents a chlorine or fluorine atom is preferred.

The enantiomerically pure or racemic compound of formula (VII) is novel and forms part of the invention.

The compound of formula (VII) in which X represents a chlorine or fluorine atom is preferred.

The compound of formula (XVI) used in stage a) of process H or in stage a) of process I is prepared from (S)- or (R)-proline according to the processes described in Tetrahedron, 1981, 37 (23), 4111–4119, and as illustrated in the examples.

During each of the above processes A to I or during the various constituent stages of these processes, the compounds of formula (I), (IIa), (IIb), (IIc), (IId), (IIe), (III), (IVa), (IVd), (IVe), (IV'd), (V), (VIa), (VIe), (VIII), (X), (XIII), (XIV), (XVII), (XVIII), (XIX) and (XX) thus obtained can subsequently be separated from the reaction medium according to conventional methods, such as extraction, crystallization, distillation or chromatography. Furthermore, the various abovementioned compounds obtained can either be isolated or can be charged directly to the following process or the following stage in the medium in which they have been obtained. Each of the processes A to I or each of the constituent stages of these processes can thus be combined for the preparation of the compounds of formula (I).

If appropriate, the compounds of formula (I), (IIa), (IIe), (IIIa), (IIIe), (IVa), (IVe), (IV'd), (VIa), (VIe), (XIII) and (XIV) thus obtained can be isolated in the free base or salt form according to conventional techniques.

These salts comprise those with inorganic or organic acids which make possible suitable separation or crystallization of the compounds of formula (I), (IIa), (IIe), (IIIa), (IIIe), (IVa), (IVe), (IV'd), (VIa), (VIe), (XIII) and (XIV), such as the hydrochloride, hydrobromide, sulfate, hydrogensulfate, dihydrogenphosphate, methanesulfonate, methyl sulfate, maleate, fumarate, succinate, naphthalene-2-sulfonate, glyconate, gluconate, citrate, isethionate, benzynesulfonate or para-toluenesulfonate.

When the compounds of formula (I), (IIa), (IIe), (IIIa), (IIIe), (IVa), (IVe), (IV'd), (VIa), (VIe), (XIII) and (XIV) are obtained in the free base form, salification is carried out by treatment with the chosen acid in an organic solvent. The corresponding salt is obtained by treatment of the free base, dissolved, for example, in an ether, such as diethyl ether, or in an alcohol, such as methanol, ethanol or propan-2-ol, or in acetone or in dichloromethane or in ethyl acetate, with a solution of the chosen acid in one of the abovementioned solvents, which salt is isolated according to conventional techniques.

Thus, for example, the hydrochloride, hydrobromide, sulfate, hydrogensulfate, dihydrogenphosphate, methanesulfonate, benzynesulfonate, para-toluenesulfonate, oxalate, maleate, succinate, fumarate or naphthalene-2-sulfonate is prepared.

The compounds of formula (I), (IIa), (IIe), (IIIa), (IIIe), (IVa), (IVe), (IV'd), (VIa), (VIe), (XIII) and (XIV) can be isolated in the form of one of their salts, for example the hydrochloride or oxalate; in this case, if necessary, the free base can be prepared by neutralization of said salt with an inorganic or organic base, such as sodium hydroxide or triethylamine, or with an alkali metal carbonate or bicarbonate, such as sodium carbonate, sodium bicarbonate, potassium carbonate or potassium bicarbonate.

According to a preferred aspect, a subject matter of the invention is processes A to I for the preparation of compound of formula (I), (IIa), (IIb), (IIc), (IId), (IIe), (IVa), (IVd), (IVe) and (V) in which X represents a chlorine atom or a fluorine atom.

According to another preferred aspect, a subject matter of the invention is compounds of formula (I), in the form of optically active salts with optically active organic acids, (II), (IV), (V), (VI), (VII), (XIII), (XIX) and (XX) in which X represents a chlorine atom or a fluorine atom.

Thus, according to the invention, the compounds of formula (I) are prepared by using the above processes A to I and by following the synthetic routes defined below and as illustrated in the examples:

synthetic route I: process F, stages a and b; then process E, stage a or stage a and b; then process C; then process A, stages a, b and c.

synthetic route II: process F, stages a and b; then process D, stages a, b and c; then process C; then process A, stages a, b.

synthetic route III: process G, stages a, b, c and d; then process C; then process A, stages a, b and c.

synthetic route IV: process H, stages a, b, c and d; then process C; then process A, stages a and b.

synthetic route V: process I, stages a, b, c, d, e and f; then process C; then process A, stages a and b.

synthetic routes VI to X: identical to synthetic routes I to V respectively but carrying out process B between process C and process A.

The following examples illustrate the invention without, however, limiting it.

In the examples below, the following abbreviations are used:
DCM: dichloromethane
THF: tetrahydrofuran
AT: ambient temperature.

The proton nuclear magnetic resonance ($^1$H NMR) spectra are recorded at 200 MHz in $d_6$-DMSO using the $d_6$-DMSO peak as reference. The chemical shifts δ are expressed in parts per million (ppm). The signals observed are expressed thus: s: singlet; d: doublet; d.d: double doublet; t: triplet; d.t.: double triplet; q: quartet; m: multiplet.

The enantiomeric purities were determined by analysis by High Performance Liquid Chromatography (HPLC) on a Chiracel OD or AD chiral phase (cellulose-based stationary phases) and by supercritical HPLC.

EXAMPLE 1

Synthetic Route I (R)-(+)-2-[2-(3,4-Difluorophenyl)morpholin-2-yl]1-ethanol, salt with L-(−)-di-para-toluoyltartaric acid.

(I): X=F

A) 2-Chloro-1-(3,4-difluorophenyl)ethanone (X): X=F; Hal=Cl; process F, stage a).

227.6 g of chloroacetyl chloride (IX: Hal=Hal'=Cl) are added over 10 minutes under a nitrogen atmosphere to a suspension of 247.7 g of aluminum chloride in 450 ml of DCM and then the yellow solution obtained is heated to reflux. 200 g of 1,2-difluorobenzene (VIII: X=F) are subsequently added dropwise over 2 hours and then the reaction mixture is maintained at reflux for 1 hour. After cooling the red-colored reaction mixture to 20° C., the latter is run onto 1 kg of ice and left stirring for 30 minutes. After separating by settling, the organic phase is removed, the aqueous phase is extracted with 500 ml of DCM, the combined organic phases are washed with 2×500 ml of water, with 500 ml of a saturated NaHCO₃ solution and with 500 ml of water, the organic phase is dried over MgSO₄ and the solvent is evaporated under vacuum. 327.6 g of the expected product are obtained in the form of a lachrymatory yellow oil.

Yield: 97.6%

¹H NMR: δ (ppm): 5.2: s: 2H, 7.6: dd: 1H, 7.8: m: 1H; 8.0: dd: 1H.

B) 1-Chloro-2-(3,4-difluorophenyl)but-3-en-2-ol (V) X=F; Hal=Cl; process F, stage b).

800 ml of a 1M solution of vinylmagnesium bromide (XI: Hal"=Br) in THF are cooled to −10° C. under a nitrogen atmosphere, a solution of 152.4 g of the compound obtained in the preceding stage in 800 ml of THF is added over 4 hours 30 minutes while maintaining the bulk temperature at −10° C., and then the reaction mixture is left stirring for 20 minutes at a temperature of −10° C. The reaction mixture is hydrolyzed by running it onto 2 liters of a saturated aqueous ammonium chloride solution and is left stirring for 30 minutes. After separating by settling, the organic phase is washed with 2×1 liter of a saturated NaCl solution and then the organic phase is filtered to remove the inorganic salts. 1.5 liters of a solution of the expected compound in THF are obtained, which solution is used directly in the following stage.

¹H NMR: δ (ppm): 3.9: dd: 2H, 5.3: dd: 2H, 5.9: s: 1H, 6.2: m: 1H; 7.3–7.5: m: 3H.

C) 1-[Benzyl(2-hydroxyethyl)amino]-2-(3,4-difluoro-phenyl)but-3-en-2-ol (IVa):

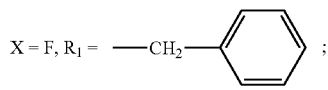

process E, stage a)

A mixture of 67.2 g of NaHCO₃ and 133 g of 2-(benzylamino)-1-ethanol in 500 ml of 1-methyl-2-pyrrolidinone is heated to 120° C. and then the solution of the compound obtained in the preceding stage in THF (1.5 liters) is run in over 3 hours while distilling off the THF from its introduction into the reaction medium. After distilling off 1.5 liters of THF, the reaction mixture is left stirring for 12 hours at 120° C. After cooling to 20° C., the reaction mixture is run onto 2 liters of water, the mixture is extracted with 2 liters of toluene and then the organic phase is washed with 2×500 ml of water. 2 liters of water are added to the organic phase, and 75 ml of a concentrated HCl solution are run in. The acidic aqueous phase is washed with 500 ml of toluene, the aqueous phase is basified by addition of 96 ml of a 10N NaOH solution and extracted with 1.2 liters of toluene, and the organic phase is washed with 500 ml of water. 1.23 kg of toluene solution comprising the expected compound are obtained, which solution is used directly in the following stage.

A dry residue from 50 g of solution comprises 8.9 g of the expected compound, i.e., with respect to the entire solution, 219 g of the expected compound.

Yield: 82%, calculated from the starting compound of stage B of formula (X): X=F; Hal=Cl.

¹H NMR: δ (ppm): 2.5: q: 2H, 2.9: s: 2H, 3.3: q: 2H, 3.6: dd: 2H, 4.5: t: 1H, 5.2: dd: 2H, 5.5: s: 1H; 6.3: dd: 1H; 7.1–7.5: m: 8H.

D) 4-Benzyl-2-(3,4-difluorophenyl)-2-vinylmorpholine maleate

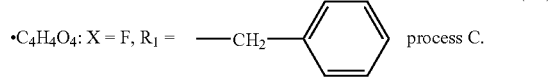

The toluene solution of the compound obtained in the preceding stage is stirred at 760 rev/min, 7.5 g of benzyltriethylammonium chloride are added and then a freshly prepared and hot solution of 215.5 g of NaOH pellets in 215 ml of water is added, the temperature of the reaction medium rising to 48° C. 139.23 g of benzenesulfonyl chloride are then added dropwise over 2 hours at a flow rate which makes it possible to maintain the bulk temperature at 45° C. After cooling the reaction mixture to 20° C., it is hydrolyzed by addition of 1 liter of water and left stirring for 1 hour. After separating by settling, the organic phase is washed with 2×1 liter of water (pH=7) and dried over MgSO₄, and the solvent is evaporated under vacuum. 200 g of the expected compound are obtained in the free base form.

Yield: 96.5%.

A suspension of 94.7 g of maleic acid in 530 ml of AcOEt is heated at reflux for 10 minutes and then a solution of 257.3 g of the free base compound (IIa: X=F) in 116 ml of AcOEt is added. The reaction mixture is allowed to return to ambient temperature and, at 43° C., crystallization is initiated by addition of 1 g of maleate of the compound (IIa: X=F) to produce rapid precipitation. The reaction mixture is cooled to 0° C. and left stirring for 12 hours. The crystallized product is filtered off, washed with 3×100 ml of cold AcOEt and dried under vacuum at 30° C. 250 g of the expected compound are obtained in the maleate form.

Yield of the salification: 71%.

¹H NMR: δ (ppm): 2.5: m: 2H, 2.9: dd: 2H, 3.7: m: 2H+2H, 5.7: dt: 2H, 5.9: dd: 1H, 6.1: s: 2H, 7.1–7.6: m: 8H.

E) 2-[4-Benzyl-2-(3,4-difluorophenyl)morpholin-2-yl]1-ethanol hydrochloride

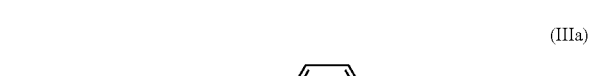

1 liter of a 0.5M solution of 9-bora-bicyclo[3.3.1]nonane in THF is introduced into a "pilot system" reactor (temperature of the oil in the jacket automatically controlled by the bulk temperature) placed under a nitrogen atmosphere and 500 ml of THF are distilled off at atmospheric pressure with a bulk temperature of 74° C. An exchange of solvent at constant volume is then carried out by introduction of 500 ml of toluene, the exchange lasting 3 hours and the final temperature being 110° C. The mass is cooled to a temperature of 20° C. and the precipitation of the dimer of 9-bora-bicyclo[3.3.1]nonane is observed. A solution of 131.4 g of the compound obtained in the preceding stage, in the free base form, in 150 ml of toluene is subsequently added over 25 minutes and the reaction mixture is left stirring for 12 hours. The reaction mixture is cooled to 5° C. and stirred at 500 rev/min, and 50 ml of a 10N NaOH solution and then 7 g of tetrabutylammonium hydrogensulfate are added. The bulk temperature preset value is adjusted to 20° C. and 60 g (53 ml) of an 11M solution of hydrogen peroxide in water (33%, 130 volumes, d=1.13) are added at a flow rate by mass of 1 g/min. The bulk preset value is then adjusted to 35° C. and 60 g of the 11M hydrogen peroxide solution are added at a flow rate by mass of 1.5 g/min. Finally, the bulk preset value is adjusted to 50° C. and 60 g of the 11M hydrogen peroxide solution are added at a flow rate by mass of 3 g/min. The mixture is left stirring for 1 hour at a temperature of 50° C. After separating by settling under warm conditions, three phases are observed: toluene/cis-1,5-cyclooctanediol/-water. After removing the aqueous phase, the mixture is cooled to 20° C. and the toluene phase is washed with 3×200 ml of water to remove the diol. The residual water is removed from the toluene phase by azeotropic entrainment at constant volume with 200 ml of toluene. 1 g of hydrochloride of the expected compound (IIIa: X=F) is then added to the clear toluene phase thus obtained and then 68 ml of a 6.1M solution of HCl in ethanol are added dropwise over 40 minutes. The mixture is cooled to 20° C. and left stirring for 3 hours, and the precipitate formed is filtered off, washed with 3×100 ml of toluene and dried under vacuum at 30° C. 124.3 g of the expected compound are obtained in the hydrochloride form.

Yield: 80.6%.

$^1$H NMR: δ (ppm): 2.0: m: 2H, 3.0: m: 2H, 3.2: m: 2H, 3.4: m: 2H, 4.0: dd: 2H, 4.4: s: 2H, 7.1–7.8: m: 8H.

F) 2-[2-(3,4-Difluorophenyl)morpholin-2-yl]-1-ethanol, racemic (I): X=F, process A, stage b).

26 g of 50% wet 10% palladium-on-charcoal are introduced into a hydrogenation reactor purged with nitrogen, then a solution of 236.3 g of the compound obtained in the preceding stage in the free base form in 2.6 liters of MeOH is run in and 53 ml of a concentrated HCl solution are added. Hydrogenation is carried out under a pressure of 3 bar at a temperature of 40° C. for 1 hour. The reaction mixture is cooled to 20° C. and filtered through a Whatman® filter paper, the filter paper is washed with 500 ml of MeOH and the filtrate is concentrated under vacuum to a volume of 500 ml. An exchange of solvent with 500 ml of water is carried out, 80 ml of 10N NaOH are then added to the aqueous solution thus obtained and the mixture is left stirring for 1 hour at 15° C. The precipitate formed is filtered off, washed with 200 ml of water, taken up in 400 ml of diisopropyl ether and left stirring for 1 hour. The precipitate is filtered off, washed with 200 ml of diisopropyl ether and dried under vacuum overnight at 40° C. 120 g of the expected product are obtained.

Yield: 78%.

G) (R)-(+)-2-[2-(3,4-Difluorophenyl)morpholin-2-yl]-1-ethanol, salt with L-(−)-di-para-toluoyltartaric acid (I): X=F; process A, stage c).

A suspension of 60 g of the compound obtained in the preceding stage in 780 ml of MeOH is heated to 40° C. It is stirred at 240 rev/min and a solution of 95.3 g of L-(−)-di-para-toluoyltartaric acid in 300 ml of MeOH is added over 50 minutes while maintaining the bulk temperature at 40° C. The reaction mixture is subsequently left stirring for 10 minutes at 40° C. and then for 1 hour at 35° C., and is cooled to 20° C. over 2 hours 30 minutes. The mixture is left stirring for 12 hours at 20° C. and the precipitate formed is filtered off, taken up in 150 ml of MeOH and left stirring for 30 minutes. The precipitate is again filtered off, washed with 60 ml of MeOH and dried under vacuum at 40° C. 64.3 g of the expected compound are obtained in the form of a salt with L-(−)-di-para-toluoyltartaric acid.

Yield: 41.3%.

Final yield: 14.2%, calculated from the starting compound of stage A of formula (VIII): X=F.

Enantiomeric purity: 97.5% (e.e.=95%).

EXAMPLE 2

Synthetic Route II (R)-(+)-2-[2-(3,4-Difluorophenyl)morpholin-2-yl]-1-ethanol.

(I): X=F.

A) 2-Chloro-1-(3,4-difluorophenyl)ethanone (X): X=F; Hal=Cl; process F, stage a).

The procedure is identical to that of stage A of example 1.

B) 1-Chloro-2-(3,4-difluorophenyl)but-3-en-2-ol (V): X=F; Hal=Cl; process F, stage b).

560 ml of a 1.8M solution of vinylmagnesium chloride (XI: Hal"=Cl) in THF are cooled to −15° C. under a nitrogen atmosphere and a solution of 170 g of the compound obtained in the preceding stage in 510 ml of THF is added over 2 hours while maintaining the bulk temperature at −15° C. The reaction mixture is hydrolyzed by running it onto 1 liter of saturated aqueous ammonium chloride solution and is left stirring for 1 hour at ambient temperature. After separating by settling, the organic phase is washed with 2×1 liter of a saturated aqueous NaCl solution. 840 ml of a solution of the expected compound in THF are obtained, which solution is used directly in the following stage.

C) 1-(Benzylamino)-2-(3,4-difluorophenyl)but-3-en-2-ol (VIa):

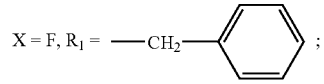

process D, stage a).

A mixture of 81 g of NaHCO$_3$ and 112.7 g of benzylamine in 190 ml of THF is heated to reflux and 300 ml of the solution of the compound obtained in the preceding stage in THF are quickly added. As soon as reflux is again reached, the THF is distilled off at constant volume while adding the remainder of the preceding solution (540 ml). At the end of the addition, the reaction mixture is concentrated to a THF volume of 400 ml. An exchange of solvent is then carried out at constant volume with 580 ml of propionitrile, the bulk temperature being 85° C. at the end of the exchange. The mixture is left stirring at 85° C. for 8 hours. The propionitrile is then removed by solvent exchange at constant volume by addition, over 4 hours 30 minutes, of 1.1 liters of toluene, the bulk temperature being 106° C. at the end of the exchange. After cooling to ambient temperature, 1.3 liters of toluene are added to produce 1.9 liters of final solution and then the toluene phase is washed with 2 liters of an aqueous solution comprising 12.5 ml of acetic acid. 1.3 liters of an aqueous solution comprising 80 ml of concentrated HCl are added to the organic phase and the volume is made up by addition of 400 ml of toluene and of the sufficient amount of water to obtain 2.5 liters of aqueous phase, in order to dissolve the oil obtained. After extraction and separation by settling, the organic phase is washed with 500 ml of water and the aqueous phases are combined. The aqueous phases are basified by the addition of 105 ml of 10N NaOH and extracted with 1.3 liters and then with 0.7 liter of diisopropyl ether, the combined organic phases are washed with 3×2 liters of water and dried over MgSO$_4$, and the solvent is evaporated under vacuum. 163 g of the expected product are obtained.

Yield: 64%, calculated from the starting compound of stage B of formula (X): X=F; Hal=Cl.

$^1$H NMR: δ (ppm): 3.2: dd: 2H, 4.1: s: 2H, 5.2–5.4: dd: 2H, 6.1–6.3: dd: 1H, 7.2–7.6: m: 8H.

D) R-(+)-1-(Benzylamino)-2-(3,4-difluorophenyl) but-3-en-2-ol, salt with L-(+)-mandelic acid (VIa):

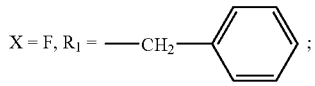

process D, stage b).

A suspension of 36.25 g of L-(+)-mandelic acid in 1.1 liters of diisopropyl ether is heated to 60° C., a solution of 137.9 g of the compound obtained in the preceding stage in 555 ml of diisopropyl ether is added over 4 hours and then, at the end of the addition, the reaction medium is heated at 75° C. for 1 hour 30 minutes to dissolve the precipitate already formed. The reaction mixture is cooled to 20° C. using a cooling slope at the rate of 0.3° C./min and is left stirring at 20° C. for 8 hours. The precipitate formed is filtered off, resuspended in 600 ml of diisopropyl ether, again filtered off and dried under vacuum at 30° C. 103 g of the expected compound are obtained. The compound is taken up in 720 ml of AcOEt and heated to 60° C. using a temperature slope at the rate of 1° C./min, and the solution obtained is kept stirred at 60° C. for 15 minutes. It is cooled to 0° C. with a cooling slope of 1° C./min, crystallization is initiated and the mixture is left stirring at 0° C. for 4 hours. The precipitate formed is filtered off, washed with 150 ml of diisopropyl ether and dried under vacuum at 30° C. 60 g of the expected compound are obtained in the form of the salt with L-(+)-mandelic acid.

Yield: 28.5%.

Enantiomeric purity: 97.4% (e.e.: 94.8%).

$\alpha_D^{25}$=+44.6° (c=1, MeOH).

E) (R)-(+)-1-[Benzyl(2-hydroxyethyl)amino]-2-(3,4-difluorophenyl)but-3-en-2-ol (IVa):

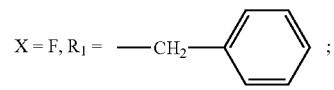

process D, stage c).

A solution of 70.25 g of the compound obtained in the preceding stage in 200 ml of MeOH is introduced into a Parr reactor, the reactor is placed under vacuum and the solution is cooled to 0° C. Ethylene oxide, preheated to 30° C., is subsequently introduced to a pressure of 1 bar and then the reaction medium is slowly heated to 40° C. and left stirring for 4 hours. After having vented off the ethylene oxide and then purged the reaction medium by bubbling with nitrogen, the MeOH is concentrated under vacuum. The residual oil is taken up in 250 ml of water, the aqueous phase is acidified by addition of 13 ml of concentrated HCl, the acidic aqueous phase is washed with 2×250 ml of methyl tert-butyl ether, and the aqueous phase is basified by addition of 18 ml of 10N NaOH and extracted with 2×250 ml of toluene. The combined organic phases are chromatographed on 500 g of silica, elution being carried out with 5×250 ml of a toluene/AcOEt (50/50; v/v) mixture. The phases are combined and the solvents are concentrated under vacuum. 43.5 g of the expected compound are obtained.

Yield: 81%.

$\alpha_D^{25}$+13.9° (c=1, MeOH).

F) (R)-(+)-4-Benzyl-2-(3,4-difluorophenyl)-2-vinyl-morpholine hydrochloride

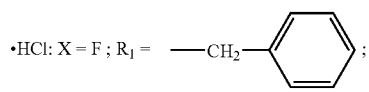

process C.

A solution of 40 g of the compound obtained in the preceding stage in 200 ml of toluene is stirred at 760 rev/min, 1.4 g of benzyltriethylammonium chloride are added and then a freshly prepared and hot solution of 40 g of NaOH pellets in 40 ml of water is added, the temperature of the reaction medium rising to 48° C. 25.43 g of benzenesulfonyl chloride are then added dropwise over 1 hour at a flow rate which makes it possible to maintain the bulk temperature at 45° C. After cooling the reaction mixture to 20° C., it is hydrolyzed by addition of 200 ml of water and is left stirring for 1 hour. After separating by settling, the organic phase is washed with 2×200 ml of water (pH=7) and dried over MgSO$_4$. 20 ml of a 6.1M solution of HCl in ethanol are added dropwise to the toluene solution thus obtained, the mixture is left stirring for 1 hour and the solvents are concentrated under vacuum. The residue is taken up in 200 ml of toluene and stirred, and the precipitate formed is filtered off. The precipitate is washed with 100 ml of toluene and is dried under vacuum at 30° C. 37 g of the expected compound are obtained in the hydrochloride form.
Yield: 87%.
$\alpha_D^{25}$ +19.7° (c=1, MeOH).

G) R-(+)-2-[4-Benzyl-2-(3,4-difluorophenyl)morpholin-2-yl]-1-ethanol hydrochloride

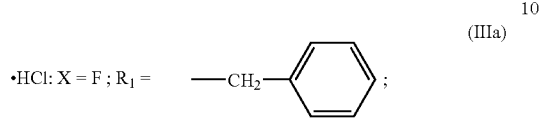

(IIIa)

•HCl: X = F ; R$_1$ =  —CH$_2$— process A, stage a)

100 ml of THF are distilled off under vacuum, under a nitrogen atmosphere, from 200 ml of a 0.5M solution of 9-borabicyclo[3.3.1]nonane in THF. A solvent exchange at constant volume is then carried out by introduction of 100 ml of toluene and then the solution obtained is cooled to 20° C. (precipitation of the dimer of 9-BBN). A solution of 30 g of the compound obtained in the preceding stage in the free base form in 35 ml of toluene is added and the mixture is left stirring for 8 hours. 11 ml of a 10N NaOH solution are subsequently added, followed by 1.6 g of tetrabutyl-ammonium hydrogensulfate dissolved in 2 ml of water. The reaction mixture is stirred at 500 rev/min and heated to a bulk temperature of 45° C., 31 g of an 11M solution of hydrogen peroxide in water (33%, 130 volumes, d=1.13) are added over 40 minutes at a flow rate which makes it possible to maintain 45° C. in the reaction medium, and the reaction medium is left stirring at 45° C. for 15 minutes. After separating by settling, the alkaline aqueous phase is removed, 100 ml of water are added to dissolve the cis-1,5-cyclooctanediol in the form of an oil, and the mixture is stirred and cooled to 20° C. After separating by settling, the organic phase is washed with 2×100 ml of water and the residual water is removed from the organic phase by azeotropic entrainment at constant volume until a clear phase is obtained. 16.4 ml of a 6.1M solution of HCl in ethanol are then added dropwise and the mixture is left stirring at 20° C. for 1 hour. The precipitate formed is filtered off, washed with 3×20 ml of toluene and dried under vacuum at 40° C. 28 g of the expected product are obtained in the hydrochloride form.
Yield: 90%.
$\alpha_D^{25}$ +41.6° (c 1, MeOH).

H) R-(+)-2-[2-(3,4-Difluorophenyl)morpholin-2-yl]-1-ethanol (I): X=F; process A, stage b).

A solution of 30 g of the compound obtained in the preceding stage in 300 ml of MeOH is added under a nitrogen atmosphere to 3 g of 50% wet 10% palladium-on-charcoal, followed by 30 ml of toluene. Hydrogenation is carried out under a pressure of 1 bar at a temperature of 30° C. The catalyst is filtered off through a Whatman® filter paper, the filter paper is washed with MeOH and then a solvent exchange is carried out on the filtrate with 120 ml of water. After cooling, the aqueous phase is washed with 2×120 ml of methyl tert-butyl ether, the aqueous phase is basified by the addition of 9 ml of 10N NaOH and the aqueous phase is left stirring for 1 hour under cold conditions. The precipitate formed is filtered off, washed with 100 ml of diisopropyl ether and dried under vacuum at 40° C. 14 g of the expected product are obtained.
Yield: 65%.
Final yield: 7.3%, calculated from the starting compound of stage A of formula (VIII): X=F.
$\alpha_D^{25}$=+21.9° (c=1, MeOH).
Enantiomeric purity: 99% (e.e. 98%).

EXAMPLE 3

Synthetic Route III (R)-(+)-2-[2-(3,4-Difluorophenyl)morpholin-2-yl]1-ethanol, salt with L-(−)-di-para-toluoyltartaric acid.
(I): X=F.

A) N-Benzyl-2-(tetrahydro-2H-pyran-2-yloxy)-1-ethyl-amine maleate

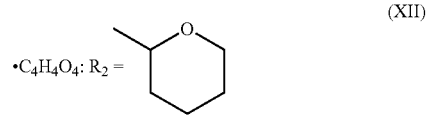

(XII)

•C$_4$H$_4$O$_4$: R$_2$ =

100 g of 2-(benzylamino)-1-ethanol are added at ambient temperature to a mixture of 110 g of benzenesulfonic acid in 1.8 liters of DCM, the temperature at the end of the addition being 34.4° C. and the pH=2. The reaction mixture is cooled to 20° C. and 105 ml of 3,4-dihydro-2H-pyran are added dropwise, the reaction mixture turning yellow, then pink and finally purple in color at the end of the addition. The mixture is poured onto 2 liters of a 10% aqueous K$_2$CO$_3$ solution, then, after separating by settling, the organic phase is dried over Na$_2$SO$_4$ and the solvent is evaporated under vacuum. The oil obtained is dissolved in 200 ml of AcOEt, a hot solution of 72.7 g of maleic acid in 655 ml of AcOEt is added and the mixture is left stirring overnight at ambient temperature. The precipitate formed is filtered off, washed with 3×100 ml of AcOEt and dried under vacuum at ambient temperature. 207 g of the expected product are obtained in the maleate form.
Yield: 89%.
$^1$H NMR: δ (ppm): 1.2–1.7: m: 6H, 3.0: t: 2H; 3.1–3.8: m: 2H, 4.1: s: 2H, 4.5: t: 1H, 7.2–7.4: m: 5H; 8.0: s: 1H.

B) 2-Chloro-1-(3,4-difluorophenyl)ethanone (X): X=F; Hal=Cl; process G, stage a).
The procedure is identical to that of stage A of example 1.

C) 2-{Benzyl[2-(tetrahydro-2H-pyran-2-yloxy)ethyl]-amino}-1-(3,4-difluorophenyl)-1-ethanone (XIII):

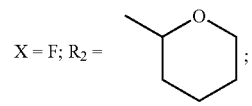

X = F; R$_2$ = process G, stage b).

1.5 liters of a 10% aqueous K$_2$CO$_3$ solution are added to a suspension of 200 g of the compound obtained in stage A in 1 liter of DCM and then, after separating by settling, the solvent is evaporated under vacuum and the oil obtained is dissolved in 250 ml of THF. This solution is added to a solution of 52.65 g of NaHCO$_3$ in 10.35 ml of water and the reaction mixture is heated to reflux. A solution of 108.55 g of the compound obtained in stage B in 250 ml of THF is then added dropwise over 50 minutes and the mixture is left stirring at reflux for 3 hours. The water is removed by azeotropic entrainment under a nitrogen atmosphere with simultaneous addition of 600 ml of THF over 2 hours. After cooling to ambient temperature, 4 angstrom molecular sieve is added to the solution and the mixture is left stirring overnight. After filtering under a nitrogen atmosphere, 800 ml of a solution of the expected compound in THF are obtained, which solution is used directly in the following stage.

$^1$H NMR: δ (ppm): 1.4: m: 6H, 2.7: dt: 1H, 3.3: m: 2H, 3.6: m: 2H, 3.7: s: 2H, 4.0: s: 2H, 4.4: m: 2H; 7.0–7.4: m: 8H.

D) 1-{Benzyl[2-(tetrahydropyran-2-yloxy)ethyl]amino}-2(3,4-difluorophenyl)but-3-en-2-ol (XIV):

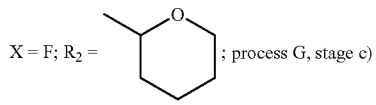

; process G, stage c)

The solution of the compound obtained in the preceding stage in THF is added over 30 minutes under a nitrogen atmosphere, at a flow rate which makes it possible to obtain a bulk temperature of 55° C., to 911 ml of a 1M solution of vinylmagnesium bromide (XI: Hal"=Br) in THF and then the reaction mixture is left stirring at 50° C. for two hours. The reaction mixture is hydrolyzed by running it onto 1.5 liters of a saturated ammonium chloride solution over 45 minutes while maintaining a bulk temperature of 30° C. 500 ml of water are added. After separating by settling, the aqueous phase is extracted with 1 liter of diisopropyl ether, the organic phases are combined and the solvents are evaporated under vacuum. 241 g of the expected compound are obtained, which is used without further treatment in the following stage.

E) 1-[Benzyl(2-hydroxyethyl)amino]-2-(3,4-difluorophenyl)but-3-en-2-ol (IVa):

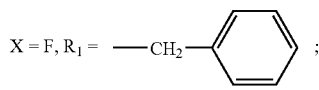

process G, stage d).

500 ml of MeOH are cooled to 5° C. and 57 ml of acetyl chloride are added dropwise while maintaining a bulk temperature of 10° C. This solution is then added, over 1 hour at ambient temperature, to a solution of 241 g of the compound obtained in the preceding stage in 500 ml of MeOH and the reaction mixture is left stirring for 2 hours at ambient temperature. The reaction mixture is concentrated under vacuum, the oily residue is dissolved with 1 liter of water, the aqueous phase is washed with 2×500 ml of diisopropyl ether, and the aqueous phase is basified by addition of 40 g of NaOH pellets and extracted with 2×800 ml of toluene. 500 ml of water and 400 ml of toluene are added to the organic phase and separation is carried out by settling. 2.083 liters of a solution of the expected compound in toluene are obtained, which solution is used directly in the following stage (content by HPLC: 91 mg/ml, i.e. a mass of 189.5 g of the compound (IVa): X=F)).

F) 4-Benzyl-2-(3,4-difluorophenyl)-2-vinylmorpholine maleate

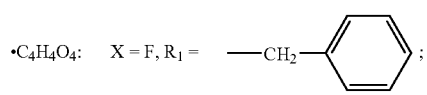

process C.

6.4 g of benzyltriethylammonium chloride are added to the toluene solution of the compound obtained in the preceding stage and then a freshly prepared and hot solution of 187 g of NaOH pellets in 187 ml of water is added, the bulk temperature being 50° C. 86 ml of benzenesulfonyl chloride are then added dropwise over 2 hours at a flow rate which makes it possible to maintain a bulk temperature of 55° C. maximum. After cooling to AT, 1 liter of water is added and the mixture is left stirring for 15 minutes. After separating by settling, the organic phase is washed with 2×1 liter of water and with 1 liter of a saturated NaCl solution. The organic phase is chromatographed on 180 g of silica and then the silica is rinsed with 400 ml of toluene. The toluene phases are combined and the solvent is concentrated under vacuum. 137.8 g of the expected compound are obtained in the free base form.

A suspension of 50.7 g of maleic acid in 284 ml of AcOEt is heated to reflux, then a solution of 137.8 g of the free base compound obtained above in 62 ml of AcOEt is added and the mixture is left stirring for 12 hours while allowing the temperature to return to AT. The mixture is cooled to 0° C. and left stirring for 1 hour, and the precipitate formed is filtered off, washed with 4×50 ml of cold AcOEt and dried under vacuum at AT. 157 g of the expected compound are obtained in the maleate form.

Yield: 60% calculated from the starting compound of stage C) of formula (X): X=F; Hal Cl.

G) 2-[4-Benzyl-2-(3,4-difluorophenyl)morpholin-2-yl]-1-ethanol hydrochloride

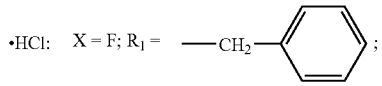

process A, stage a).

500 ml of water are added to a suspension of 245.3 g of the compound obtained in the preceding stage in 500 ml of toluene, and then 120 ml of a 10N sodium hydroxide solution are run in. After separating by settling, the aqueous phase is extracted with 500 ml of toluene, the organic phases are combined and the water is removed by azeotropic entrainment at constant volume with addition of toluene. The toluene solution is concentrated to a volume of 350 ml.

800 ml of a 0.5M solution of 9-borabicyclo-[3.3.1]nonane in THF are introduced into a "pilot system" reactor placed under a nitrogen atmosphere and the solution is concentrated at atmospheric pressure to a volume of 400 ml. 600 ml of the 0.5M solution of 9-BBN in THF are again added and the solution is reconcentrated to a volume of 700 ml of THF. A solvent exchange is then carried out at constant volume by introduction of 700 ml of toluene, the bulk temperature changing from 68° C. to 110° C. The mass is cooled to 20° C. and precipitation of the dimer of 9-BBN is observed. The 350 ml solution of the compound (IIa): X=F, prepared above is subsequently added and the mixture is left stirring for 8 hours. The reaction mixture is cooled to 5° C. and 9.6 g of tetrabutylammonium hydrogensulfate and then 69 ml of 10N NaOH solution are added. The bulk temperature preset value is adjusted to 20° C. and 72.3 g of an 11M solution of hydrogen peroxide in water (33%, 130 volumes, d=1.13) are added at a flow rate by mass of 1.2 g/min. The bulk preset value is then adjusted to 35° C. and 72.3 g of the 11M hydrogen peroxide solution are added at a flow rate by mass of 1.8 g/min. Finally, the bulk preset value is adjusted to 50° C. and 72.3 g of the 11M hydrogen peroxide solution are added at a flow rate by mass of 3 g/min. The mixture is left stirring for 1 hour at 50° C., separation by settling is carried out under warm conditions and 3 phases are obtained: toluene/cis-1,5-cyclooctanediol/water. The aqueous phase is removed, the toluene phase is washed with 2×200 ml of water to remove the diol, then the organic phase is cooled to 20° C. and the organic phase is dried over $Na_2SO_4$. 95 ml of a 6.1M solution of HCl in ethanol are added to the organic phase, initiation is carried out by addition of 1 g of hydrochloride of the compound (IIIa: X=F) and the mixture is left stirring at AT for 3 hours. The precipitate formed is filtered off, washed with 3×250 ml of toluene and dried under vacuum at AT. 164 g of the expected compound are obtained in the hydrochloride form.

Yield: 86%.

H) 2-[2-(3,4-Difluorophenyl)morpholin-2-yl]-1-ethanol, racemic (I): X=F; process A, stage b).

16 g of 50% wet 10% palladium-on-charcoal are introduced into a hydrogenation reactor placed under a nitrogen atmosphere and then a solution of 164 g of the compound obtained in the preceding stage in the hydrochloride form in 1.6 liters of NaOH is carefully poured in. The mixture is hydrogenated under a pressure of 3 bar at 40° C. for 3 hours. After cooling to AT, the catalyst is filtered off on a Whatman® filter paper, the filter paper is washed with 100 ml of MeOH, 55 ml of 10N NaOH are added to the filtrate and the MeOH is concentrated under vacuum to a volume of 200 ml. A solvent exchange is carried out with water by azeotropic entrainment. After having removed all the MeOH, the mixture is left stirring for 1 hour and the precipitate formed is filtered off, washed with 2×100 ml of water and dried under vacuum overnight at 40° C. 102 g of the expected compound are obtained.

Yield: 94.8%.

I) (R)-(+)-2-[2-(3,4-Difluorophenyl)morpholin-2-yl]-1-ethanol, salt with L-(−)-di-para-toluoyltartaric acid (I): X=F; process A, stage c).

A suspension of 95 g of the compound obtained in the preceding stage in 1.235 liters of MeOH is heated to 40° C. and a solution of 150.88 g of L-(−)-di-para-toluoyltartaric acid in 475 ml of MeOH is added over 1 hour. When half of this solution has been run in, initiation is carried out by addition of 0.4 g of resolved salt and, when the solution has finished being run in, the mixture is left stirring for 4 hours 30 minutes while allowing the temperature to return to AT. The mixture is cooled to 20° C. and stirring continued for 2 hours, and the precipitate formed is filtered off, washed with 2×100 ml of EtOH and dried under vacuum at AT. 100 g of the expected compound are obtained in the form of the salt with L-(−)-di-para-toluoyltartaric acid.

Yield: 40.8%.

Final yield: 19.5%, calculated from the starting compound of stage B) of formula (VIII): X=F.

Enantiomeric purity: 97.4% (e.e. =94.8%).

EXAMPLE 4

Synthetic Route IV (S)-(−)-2-[2-(3,4-Difluorophenyl)morpholin-2-yl]-1-ethanol.

(I): X=F.

A) Methyl 2-phenylhexahydro-1H-pyrrolo[1,2-c] imidazole-3-carboxylate, single isomer (XVI)

a) (S)-1-[(Benzyloxy)carbonyl]proline

This compound is commercially available.

b) Benzyl (S)-2-(anilinocarbonyl)-1-pyrrolidine-carboxylate 9.7 ml of N-methylmorpholine are added under a nitrogen atmosphere to a solution of 20 g of the compound obtained in the preceding stage in 200 ml of actetonitrile, this solution is then cooled to 0° C. and 7.7 ml of ethyl chloroformate are added over 45 minutes. The reaction medium is cooled to 0° C. and 7.3 ml of aniline are added over 45 minutes. The reaction mixture is concentrated under vacuum, the oily residue is extracted with 200 ml of AcOEt, the organic phase is washed with 2×200 ml of a pH=2 buffer solution, with 200 ml of water and with 2×200 ml of a 10% aqueous $NaHCO_3$ solution, 200 ml of ACOEt are added to the organic phase, then the organic phase is dried over $Na_2SO_4$ and filtered, and the solvent is concentrated under vacuum. The residue is taken up in 100 ml of tert-butyl methyl ether and the mixture is left stirring for 1 hour, and the precipitate formed is filtered off, washed with 20 ml of tert-butyl methyl ether and dried under vacuum at 40° C. 20.8 g of the expected product are obtained.

Yield: 80%.

$^1$H NMR: δ (ppm): 1.8: m: 2H, 2.2: m: 2H, 3.5: m: 2H, 4.3: d.t: 1H, 4.9: d: 1H, 5.1: d: 1H, 7.0–7.4: m: 8H, 8.6: m: 2H; 10: d: 1H.

c) (S)-N-Phenyl-2-pyrrolidinecarboxamide

A solution of 20 g of the compound obtained in the preceding stage and 5.3 ml of concentrated HCl in 300 ml of MeOH is carefully poured under a nitrogen atmosphere onto 2 g of 50% wet 10% palladium-on-charcoal and hydrogenation is carried out for 2 hours at atmospheric pressure and at AT. 5 ml of concentrated HCl are added, the catalyst is filtered off and the filtrate is concentrated under vacuum. The residue is dissolved in 200 ml of water, the aqueous phase is washed with 200 ml of AcOEt, the aqueous phase is basified by the addition of 5 g of NaOH pellets and extracted with 3×200 ml of DCM. The DCM is removed by azeotropic entrainment with THF and then the THF is evaporated under vacuum. 11.5 g of the expected product are obtained.

Yield: 94.5%.

$^1$H NMR: δ (ppm): 1.7: m: 2H, 2.0: m: 2H, 2.9: t: 2H, 3.3: s: 1H, 3.7: m: 1H, 7.1: d.d: 1H, 7.3: d.d: 1H; 7.7: d: 2H, 9.9: s: 1H.

d) (S)-N-(2-Pyrrolidinylmethyl)aniline 80 ml of a 1M solution of lithium aluminum hydride in THF are heated to reflux under a nitrogen atmosphere and a solution of 12 g of the compound obtained in the preceding stage in 120 ml of THF is slowly added. The reaction mixture is allowed to return to AT, 3 ml of water, 3 ml of 10N NaOH and 9 ml of water are carefully added, and the mixture is left stirring overnight at AT. The mixture is filtered and the filtrate is concentrated under vacuum. The oil obtained is distilled under vacuum (B.p.=158–164° C./1 mbar). 8.6 g of the expected product are obtained.

Yield: 76%.

$^1$H NMR: δ (ppm): 1.1: m: 2H, 1.6: m: 2H, 2.6–2.8: m: 4H, 3.1: m: 1H, 5.3: t: 1H, 6.4: m: 3H, 7.0: m: 2H.

e) Methyl 2-phenylhexahydro-1H-pyrrolo[1,2-c]-imidazole-3-carboxylate, single isomer 1.89 g of methyl hydroxymethoxyacetate are added to a solution of 2.64 g of the compound obtained in the preceding stage in 25 ml of toluene and then the mixture is heated at reflux for 1 hour 30 minutes while azeotropically removing the water formed. The reaction mixture is allowed to return to AT, 25 ml of water are added to dissolve the insoluble materials, the organic phase is dried over MgSO$_4$ and the solvent is evaporated under vacuum. 3.67 g of the expected product are obtained.

Yield: quantitative.

$^1$H NMR: δ (ppm): 1.4–2.0: m: 4H, 2.6: m: 1H, 3.1: m: 2H, 3.5: m: 1H; 3.6: s: 3H, 3.8: m: 1H, 4.8: s: 1H; 6.4: d.d: 2H, 6.6: dd: 1H; 7.1: dd: 2H.

B) (3,4-Difluorophenyl)(2-phenylhexahydro-1H-pyrrolo[1,2-c]imidazol-3-yl)methanone, single isomer (XVII): X=F; process H, stage a).

A solution of 3,4-difluorophenylmagnesium bromide (XV: X=F; Hal'''=Br) is prepared from 0.85 g of magnesium turnings, 4 g of 1-bromo-3,4-difluorobenzene and 20 ml of THF and this solution is stored at AT.

Furthermore, 0.13 ml of 1,2-dichloroethane is added under a nitrogen atmosphere to a mixture of 0.4 g of magnesium turnings in 20 ml of THF and the mixture is heated until it becomes cloudy and gaseous ethylene is given off. 1.17 ml of 1,2-dichloroethane are then added in portions of 0.13 ml and the mixture is heated at reflux for 1 hour. This suspension of anhydrous MgCl$_2$ thus obtained is allowed to return to AT, a solution of 3.67 g of the compound obtained in stage A) in 37 ml of THF is added, and the mixture is heated at reflux for 1 hour and is allowed to return to AT. This solution is then cooled to –70° C., 20.4 ml of the solution of 3,4-difluorophenylmagnesium bromide prepared above are added while maintaining a bulk temperature of –70° C., and the mixture is left stirring at –70° C. for 1 hour. The reaction mixture is poured onto 30 ml of a saturated NH$_4$Cl solution and is left stirring for 15 minutes. The THF is concentrated under vacuum, the residue is taken up in 50 ml of diisopropyl ether, the organic phase is washed with 30 ml of water and with 30 ml of a saturated NaCl solution and dried over MgSO$_4$, and the solvent is concentrated under vacuum. 4.59 g of the expected product are obtained.

Yield: 85%.

C) 1-(3,4-Difluorophenyl)-1-(2-phenylhexahydro-1H-pyrrolo[1,2-c]imidazol-3-yl)-2-propen-1-ol, single isomer (XVIII): X=F; process H, stage b).

A solution of 4.59 g of the compound obtained in the preceding stage in 30 ml of THF is cooled to –70° C., 28 ml of a 1M solution of vinylmagnesium bromide (XI: Hal'''=Br) in THF are slowly added while maintaining a bulk temperature of –70° C., and the mixture is left stirring at –70° C. for 1 hour. The reaction mixture is poured onto 30 ml of a saturated NH$_4$Cl solution, the phases are separated by settling and the solvent of the organic phase is concentrated under vacuum. The residue is extracted with 70 ml of diethyl ether, the organic phase is washed with 30 ml of water and this organic phase is used directly in the following stage.

D) 2-(3,4-Difluorophenyl)-2-hydroxybut-3-enal, single isomer (XIX): X=F; process H, stage c).

The ethereal solution obtained in the preceding stage is cooled to 5° C., 174 ml of 2% HCl are added and the mixture is left stirring overnight at 5° C. The organic phase is washed with 30 ml of water and dried over MgSO$_4$, and the solvent is concentrated under vacuum. 2.67 g of the expected product are obtained.

Yield: 96% (calculated from the starting compound of stage C of formula (XVII): X=F.

E) (S)-(−)-1-[Benzyl(2-hydroxyethyl)amino]-2-(3,4-difluorophenyl)but-3-en-2-ol (IV):

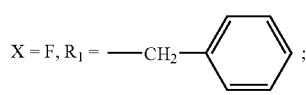

process H, stage d).

1.2 ml of 2-(benzylamino)-1-ethanol are added to a solution of 1.7 g of the compound obtained in the preceding stage in 34 ml of acetonitrile, followed by 3.63 g of sodium triacetoxyborohydride and 3 drops of acetic acid, and the mixture is left stirring for 1 hour at AT. The reaction mixture is hydrolyzed by addition of 50 ml of 1.2M HCl, the organic phase is concentrated under vacuum, the aqueous phase is washed with 50 ml of diisopropyl ether, the aqueous phase is basified by addition of 7 ml of 10N NaOH and extracted with 50 ml of diisopropyl ether, the organic phase is washed with 2×50 ml of water and dried over $MgSO_4$, and the solvent is evaporated under vacuum. 1 g of the expected product is obtained.

Yield: 35%.

Enantiomeric purity: 99.4% (e.e. =98.8%).

F) (S)-(−)-4-Benzyl-2-(3,4-difluorophenyl)-2-vinyl-morpholine (IIa):

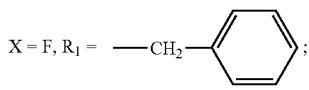

process C.

0.04 g of benzyltriethylammonium chloride is added to a solution of 1.2 g of the compound obtained in the preceding stage in 12 ml of toluene and then a freshly prepared and hot solution of 2.34 g of NaOH pellets in 2.4 ml of water is added, the temperature of the medium rising to 45° C. 0.55 ml of benzenesulfonyl chloride is then added while maintaining the temperature at 50° C. After cooling to AT, 10 ml of water are added and the mixture is left stirring for 1 hour. After separating by settling, the organic phase is washed with 2×50 ml of water and dried over $Na_2SO_4$, and the solvent is evaporated under vacuum. The residue is chromatographed on 60 g of silica, elution being carried out with the cyclohexane/diethyl ether (90/10, v/v) mixture. 0.8 g of the expected product is obtained.

Yield: 70%.

G) (S)-(−)-(2-[4-Benzyl-2-(3,4-difluorophenyl)-morpholin-2-yl)-1-ethanol (IIIa):

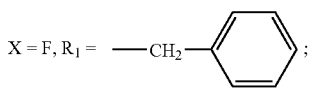

process A, stage a)

6 ml of a 0.5M solution of 9-borabicyclo[3.3.1]nonane in THF are added under a nitrogen atmosphere to 0.8 g of the compound obtained in the preceding stage, the bulk temperature is brought to 25° C. and the mixture is left stirring for 24 hours. 6 ml of THF are added, the reaction mixture is cooled to 0° C., the addition is carried out, in portions of 5×0.2 ml, of a solution comprising 1 ml of an 11M solution (130 volumes) of hydrogen peroxide in water and 0.64 g of NaOH pellets, and the mixture is left stirring for 15 minutes at AT. The THF is concentrated under vacuum, the mixture is extracted with 10 ml of toluene, the organic phase is washed with 2×10 ml of water and dried over $MgSO_4$, and the solvent is evaporated under vacuum. The oil obtained is chromatographed on 20 g of silica, elution being carried out with the DCM/diethyl ether (73/3, v/v) mixture. 0.78 g of the expected product is obtained.

Yield: 93%.

H) (S)-(−)-2-[2-(3,4-Difluorophenyl)morpholin-2-yl]-1-ethanol (I): X=F; process A, stage b).

The addition is carried out under a nitrogen atmosphere, to 0.078 g of 50% wet 10% palladium-on-charcoal, of a solution of 0.78 g of the compound obtained in the preceding stage in 10 ml of MeOH and 0.195 ml of concentrated HCl. Hydrogenation is carried out for 2 hours at atmospheric pressure and at AT. The catalyst is filtered off and the filtrate is concentrated under vacuum. 0.5 g of the expected product is obtained.

Yield: 85%.

Enantiomeric purity: 99.95%.

EXAMPLE 5

Synthetic Route V (S)-(−)-2-[2-(3,4-Difluorophenyl)morpholin-2-yl)-1-ethanol.

(I): X=F.

A) 2-(3,4-Difluorophenyl)-2-hydroxybut-3-enal, single isomer

This compound is prepared by using the procedures of stages A, B, C and D of EXAMPLE 4.

B) 2-(3,4-Difluorophenyl)but-3-ene-1,2-diol, single isomer (XX): X=F; process I, stage d).

A solution of 3.2 g of the compound obtained in the preceding stage in 110 ml of toluene is cooled to 0° C. and a solution of 0.3 g of sodium borohydride in 10 ml of EtOH is added dropwise. The reaction mixture is hydrolyzed with addition of 100 ml of a saturated $NH_4Cl$ solution, the organic phase, after separating by settling, is washed with 3×30 ml of water and dried over $MgSO_4$, and the solvent is evaporated under vacuum. The oily residue is chromatographed on silica gel, elution being carried out with the DCM/diethyl ether (90/10, v/v) mixture. 1 g of the expected product is obtained.

Yield: 31%.

C) 2-(3,4-Difluorophenyl)-2-vinyloxirane, single isomer (VII): X=F; process I, stage e).

A solution of 1 g of the compound obtained in the preceding stage and 0.04 g of benzyltriethyl-ammonium chloride in 5 ml of DCM is added to a solution of 2 g of NaOH pellets in 2 ml of water and then 0.91 g of benzene-sulfonyl chloride is run in at AT, the bulk temperature rising to 35° C. 5 ml of DCM are added and the mixture is left stirring for 30 minutes. The reaction mixture is hydrolyzed by addition of 20 ml of water and diluted with 20 ml of DCM. After separating by settling, the organic phase is washed with 4×10 ml of water and dried over MgSO$_4$, and the solvent is evaporated under vacuum. 0.91 g of the expected product is obtained.

Yield: quantitative.

D) (S)-(−)-1-[Benzyl(2-hydroxyethyl)amino]-2-(3,4-difluorophenyl)but-3-en-2-ol (IVa):

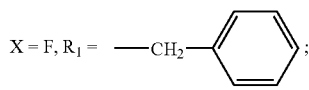

process I, stage f).

0.742 g of 2-(benzylamino)-1-ethanol is added to a solution of 0.894 g of the compound obtained in the preceding stage in 4.5 ml of acetonitrile and then the mixture is heated at reflux for 24 hours. The reaction mixture is concentrated under vacuum, the residue is taken up in 20 ml of toluene, and the organic phase is washed with 3×10 ml of water, acidified by addition of 20 ml of 0.5N HCl and extracted with 10 ml of water. The acidic aqueous phase is washed with 10 ml of toluene, basified by addition of 0.41 g of NaOH pellets and extracted with 20 ml of toluene, the organic phase is washed with 3×10 ml of water and dried over MgSO$_4$, and the solvent is evaporated under vacuum. 0.99 g of the expected product is obtained.

Yield: 60%.

Enantiomeric purity: 98.8% (e.e. 97.6%).

E) (S)-(−)-2-[2-(3,4-Difluorophenyl)morpholin-2-yl]-1-ethanol (I): X═F; process C and then process A, stages a) and b).

The preparation is carried out as in stages F, G and H of EXAMPLE 4, starting from the compound obtained in the preceding stage, and the expected product is obtained.

EXAMPLE 6

Synthetic Route VI (R)-(+)-2-[2-(3,4-Difluorophenyl)morpholin-2-yl]-1-ethanol, salt with L-(−)-di-para-toluoyltartaric acid.

(I): X═F.

A) 4-Benzyl-2-(3,4-difluorophenyl)-2-vinylmorpholine maleate, (IIa),

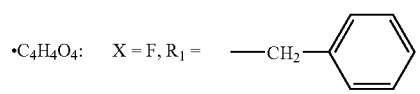

This compound is prepared by using the procedures of stages A, B, C and D of example 1.

B) Benzyl 2-(3,4-difluorophenyl)-2-vinylmorpholine-4-carboxylate (IIa):

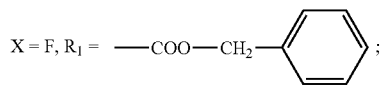

process B.

A mixture of 41.98 g of the compound obtained in stage A in the free base form (oil) and 6.55 g of K$_2$CO$_3$ is heated to 60° C., 28.68 g of benzyl chloroformate are then added dropwise over 25 minutes under a nitrogen atmosphere, and the mixture is left stirring for 5 hours at 20° C. 100 ml of toluene and 70 ml of water are added to the still hot reaction mixture, then the organic phase, after separating by settling, is washed with water and dried over MgSO$_4$, and the solvent is concentrated under vacuum. 64 g of the expected product are obtained, which product is used as is in the following stage.

C) Benzyl 2-(3,4-difluorophenyl)-2-(2-hydroxyethyl)-morpholine-4-carboxylate (IIIb):

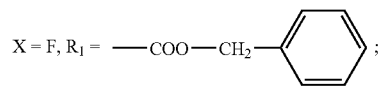

process A, stage a).

A solution of 6.35 g of trimethylsilyl hloride in 8 ml of THF is added under a nitrogen atmosphere over 15 minutes to a mixture of 2.21 g of sodium borohydride in 50 ml of THF and the mixture is left stirring at AT for 30 minutes. A solution of 7.17 g of the compound obtained in the preceding stage in 11 ml of THF is subsequently added dropwise and the mixture is left stirring at AT for 1 hour, then heated at reflux for 1 hour and left stirring overnight while allowing the temperature to return to AT. 1.05 ml of water are carefully added dropwise to the reaction mixture and then the THF is concentrated under vacuum. The residue is taken up in 60 ml of toluene, 0.24 g of tetrabutylammonium hydrogensulfate is added, 5.4 ml of 10N NaOH are then slowly added and, subsequently, 3.8 ml of an 11M solution of hydrogen peroxide in water (33%, 130 volumes, d=1.13) are added, the bulk temperature reaching 45° C. After stirring for 15 minutes, 60 ml of water are added to the reaction mixture, the organic phase, after separating by settling, is washed twice with water (pH=7) and dried over MgSO$_4$, and the solvent is evaporated under vacuum. 4.83 g of the expected product are obtained, which product is used as is in the following stage.

D) 2-[2-(3,4-Difluorophenyl)morpholin-2-yl]-1-ethanol, racemic (I): X=F; process A, stage b).

A solution of 0.77 g of the compound obtained in the preceding stage in 2.3 ml of toluene is added under a nitrogen atmosphere to 0.05 g of 50% wet 10% palladium-on-charcoal. Hydrogenation is carried out for 2 hours 30 minutes at atmospheric pressure and at 40° C. After cooling to AT, water is added to the mixture, and the mixture is acidified by addition of 0.105 ml of concentrated HCl and filtered. After separating by settling, the acidic aqueous phase is washed with toluene, basified by addition of 0.141 ml of 10N NaOH and left stirring at AT for 1 hour. The precipitate formed is filtered off, washed with water and dried under vacuum at 60° C. 0.17 g of the expected product is obtained.

E) (R)-(+)-2-[2-(3,4-Difluorophenyl)morpholin-2-yl]-1-ethanol, salt with L-(−)-di-para-toluoyltartaric acid (I): X=F; process A, stage c).

The preparation is carried out as in stage G of EXAMPLE 1, starting from the compound obtained in the preceding stage, and the expected product is obtained.

The invention claimed is:
1. A process for the preparation of a compound, in the enantiomerically pure form, of formula

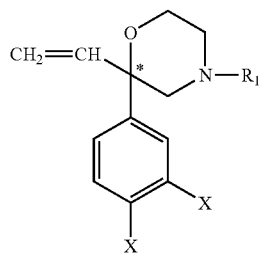
(I)

in which X represents a halogen atom, in the form of a salt, with optically active organic acids wherein:
a) a compound, in the racemic form, in the form of a mixture of diastereoisomers or in the enantiomerically pure form, of formula:

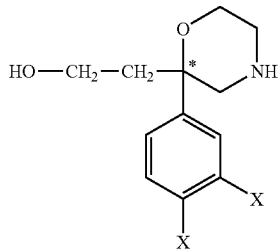
(II): (IIa):

R₁ = —CH₂—⌬ (phenyl)

(IIb):

R₁ = —COO—CH₂—⌬

(IIc):

R₁ = —COOCHClCH₃

(IId):

R₁ = —COO—C(CH₃)₃

(IIe):

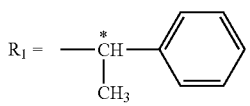

in which X is as defined for a compound of formula (I) and R₁ represents an N-protecting group chosen from a benzyl group, a benzyloxycarbonyl group, a 1-chloro-ethyloxycarbonyl group, a tert-butyloxycarbonyl group or an α-methylbenzyl group, is converted to a compound, in the racemic form, in the form of a mixture of diastereoisomers or in the enantiomerically pure form, of formula:

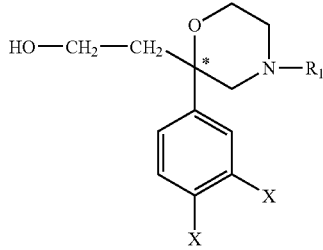
(III): (IIIa):

R₁ = —CH₂—⌬

(IIIb):

R₁ = —COO—CH₂—⌬

(IIIc):

R₁ = —COOCHClCH₃

(IIId):

R₁ = —COO—C(CH₃)₃

(IIIe):

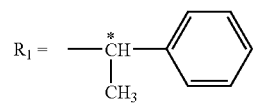

b) the compound of formula (III) thus obtained is deprotected;

c) if appropriate, when the compound of formula (I) thus obtained is in the racemic form the enantiomers are separated, and the enantiomerically pure compound of formula (I) is converted to one of its salts with optically active organic acids.

2. The process as claimed in claim 1 wherein compounds of formula (I) in which X represent a chlorine atom or a fluorine atom are prepared.

* * * * *